US011854706B2

(12) United States Patent
Peri et al.

(10) Patent No.: US 11,854,706 B2
(45) Date of Patent: Dec. 26, 2023

(54) MATERNAL AND INFANT HEALTH INSIGHTS AND COGNITIVE INTELLIGENCE (MIHIC) SYSTEM AND SCORE TO PREDICT THE RISK OF MATERNAL, FETAL AND INFANT MORBIDITY AND MORTALITY

(71) Applicant: COGNITIVECARE INC., Milpitas, CA (US)

(72) Inventors: Venkat Narasimham Peri, Plano, TX (US); Suresh Venkata Satya Attili, Hyderabad (IN); Santosh Yogendra Shah, Mumbai (IN); Venkatesh S. Sista, Visakhapatnam District (IN); Naresh Nelaturi, Visakhapatnam District (IN); Manoj Ramesh Teltumbade, Visakhapatnam District (IN); Satya Pavitra Rani, Visakhapatnam District (IN)

(73) Assignee: COGNITIVECARE INC., Milpitas, CA (US)

( * ) Notice: Subject to any disclaimer, the term of this patent is extended or adjusted under 35 U.S.C. 154(b) by 433 days.

(21) Appl. No.: 16/703,790

(22) Filed: Dec. 4, 2019

(65) Prior Publication Data
US 2021/0118574 A1 Apr. 22, 2021

(51) Int. Cl.
*G16H 50/70* (2018.01)
*G16H 15/00* (2018.01)
(Continued)

(52) U.S. Cl.
CPC ......... *G16H 50/70* (2018.01); *G06F 16/904* (2019.01); *G06F 16/95* (2019.01); *G06N 5/04* (2013.01);
(Continued)

(58) Field of Classification Search
CPC .................................................... G16H 50/30
See application file for complete search history.

(56) References Cited

U.S. PATENT DOCUMENTS 6,254,537 B1 * 7/2001 Nguyen ............. A61B 5/02411
128/920
2003/0187364 A1 * 10/2003 Hamilton ........... A61B 5/02411
600/511
(Continued)

FOREIGN PATENT DOCUMENTS

KR 20140065710 A * 5/2014

OTHER PUBLICATIONS

Liu et al., Entity recognition from clinical texts via recurrent neural network, 2017, BMC Medical Informatics and Decision Making 17 (Year: 2017).*

(Continued)

*Primary Examiner* — Karen A Hranek
(74) *Attorney, Agent, or Firm* — Dave Law Group LLC; Raj S. Dave

(57) ABSTRACT

The MIHIC system in various embodiments described herein helps clinicians predict the risk of maternal mortality by detecting diseases early and identifying possible risks in mothers, fetuses and infants across pre, peri and post-natal stages of pregnancy. The system quantifies risk as a single MIHIC score, which through quantification assigns possible risks to the mother, fetus and infant. The MIHIC score uses a specialized algorithm to derive the individual and overall risk as a value between 0 and 1 and uses the risk scores to stratify the patients into High, Medium and Low risk for preventive intervention and improved pregnancy outcome.

20 Claims, 16 Drawing Sheets

(51) Int. Cl.
  *G16H 20/00* (2018.01)
  *G16H 50/30* (2018.01)
  *G16H 10/40* (2018.01)
  *G16H 70/60* (2018.01)
  *G06N 5/04* (2023.01)
  *G06F 16/904* (2019.01)
  *G06F 16/95* (2019.01)
  *G06N 20/00* (2019.01)

(52) U.S. Cl.
  CPC ............ *G06N 20/00* (2019.01); *G16H 10/40* (2018.01); *G16H 15/00* (2018.01); *G16H 20/00* (2018.01); *G16H 50/30* (2018.01); *G16H 70/60* (2018.01)

(56) References Cited

U.S. PATENT DOCUMENTS

| | | | | |
|---|---|---|---|---|
| 2010/0312070 | A1* | 12/2010 | Rottem | G16H 70/60 600/300 |
| 2013/0073319 | A1* | 3/2013 | Du | G06Q 40/08 705/4 |
| 2015/0213225 | A1* | 7/2015 | Amarasingham | G16Z 99/00 705/2 |
| 2015/0234999 | A1* | 8/2015 | Hu | G16Z 99/00 705/2 |
| 2016/0253461 | A1* | 9/2016 | Sohr | C25B 3/25 705/3 |
| 2017/0177822 | A1* | 6/2017 | Fogel | G16H 50/70 |
| 2017/0308662 | A1* | 10/2017 | Hamilton | G16H 80/00 |
| 2018/0114600 | A1* | 4/2018 | Roberts | G16B 30/00 |
| 2018/0253810 | A1* | 9/2018 | Edmund | G06F 40/263 |
| 2018/0277248 | A1* | 9/2018 | Nazem | G16H 50/30 |
| 2019/0034589 | A1* | 1/2019 | Chen | G06N 3/0454 |
| 2019/0072564 | A1* | 3/2019 | Jelliffe | G16H 50/20 |
| 2019/0108912 | A1* | 4/2019 | Spurlock, III | G06Q 10/10 |
| 2019/0122770 | A1* | 4/2019 | Pengetnze | G06N 5/04 |
| 2020/0073639 | A1* | 3/2020 | Prasad | G06F 8/10 |
| 2021/0057039 | A1* | 2/2021 | Brohman | G16H 10/40 |
| 2021/0098133 | A1* | 4/2021 | Chowdhry | G16H 10/60 |
| 2021/0383913 | A1* | 12/2021 | Tablan | G10L 15/26 |
| 2022/0181020 | A1* | 6/2022 | Keshavjee | G06F 3/013 |

OTHER PUBLICATIONS

Yamashita et al., Convolutional neural networks: an overview and application in radiology, Jun. 2018, Insights into Imaging (Year: 2018).*

Deepa & Lalwani, Image Classification and Text Extraction using Machine Learning, Jun. 2019, Proceedings of the Third International Conference on ELectronics Communication and Aerospace Technology (Year: 2019).*

Tobore et al., Deep Learning Intervention for Health Care Challenges: Some Biomedical Domain Considerations, Aug. 2019, JMIR mHealth and uHealth 7(8) (Year: 2019).*

Catley et al., Predicting Preterm Birth Using Artificial Neural Networks, 2005, 18th IEEE Symposium on Computer-Based Medical Systems (Year: 2005).*

Moreira et al., A Preterm Birth Risk Prediction System for Mobile Health Applications Based on the Support Vector Machine Algorithm, 2018, IEEE (Year: 2018).*

Podda et al., A machine learning approach to estimating preterm infants survivial: development of the Preterm Infants Survival Assessment (PISA) predictor, Sep. 2018, Scientific Reports (Year: 2018).*

Tahir et al., Neural Networks Algorithm to Inquire Previous Preeclampsia Factors in Women with Chronic Hypertension During Pregnancy in Childbirth Process, 2018, IEEE (Year: 2018).*

Moreira et al., Fetal Birth Weight Estimation in High-risk Pregnancies through Machine Learning Techniques, May 2019, IEEE (Year: 2019).*

Teixeira, Social Media and Chatbots use for chronic disease patients support: case study from an online community regarding therapeutic use of cannabis, Jul. 2019, Mestrado em Multimedia da Universidade do Porto (Year: 2019).*

* cited by examiner

MATERNAL AND INFANT HEALTH INSIGHTS AND COGNITIVE INTELLIGENCE (MIHIC) SYSTEM AND SCORE TO PREDICT THE RISK OF MATERNAL, FETAL AND INFANT MORBIDITY AND MORTALITY

TECHNICAL FIELD OF THE INVENTION

The field in general relates to risk assessment of maternal, fetal and infant health and preventive treatment in pregnant women, fetuses and infants. Particularly it relates to the determination of pregnancy related risk factors in a woman while pregnant and upon childbirth and accordingly devices preventive treatment strategies and/or personalized medicine to the at-risk mother/fetus/infant.

BACKGROUND

Preventive and personalized medicine are critical in improving healthcare delivery. Ability to prevent a disease is predicated upon identifying all the possible risks that can lead to the manifestation of that particular disease. These insights about possible risks can then be used by caregivers, payers and policy makers to identify the individuals and populations with higher maternal risk and use these insights to determine the intervention to either prevent the disease or management of treatment for disease (if it can't be prevented completely). As an example, if all the pregnant mothers with high risk of pre-term eclampsia can be identified, then the Clinicians and payers can work in conjunction to define a pro-active approach comprising of clinical (specific drugs, recommending more suitable care facilities, more frequent monitoring of bio-markers etc.) and/or non-clinical interventions (specific changes to life-style etc.) to ensure the risk is eliminated or mitigated significantly.

The ability to determine the risks in an individual patient will depend on the ability to bring as many data points as possible about the patient including, but not limited to: patient's health history, genetics, life-style data, socio-economic data, Clinician-patient interactions (notes, audios, videos), epidemiology data, environmental and social media data. It is imperative that such comprehensive analyses of data can be carried out using advanced computing capabilities including Artificial Intelligence (Natural Language processing, neural networks, deep learning etc.), Quantum Mechanics, Re-enforcement learning and advanced mathematics (graph theory, Ricci flows etc.) to process/analyze these vast amounts of diverse data and detect possible patterns of correlation and causality. These insights, when quantified as easily readable risk scores, can help caregivers and policy makers to detect the possible patterns that can lead to high risk of disease manifestation and progress in patients but also help them to recommend treatments.

The continued success of these solutions will also depend on how successfully the system can learn and adopt the real-time feed-back and incorporate it for future predictions.

According to the World Health Organization's report, Maternal mortality around the world is an unacceptably high 830 deaths per day, resulting from pregnancy or childbirth-related complications (WHO Report "Global Health Observatory (GHO) data-Maternal and reproductive health" 2015). Though a number of countries in sub-Saharan Africa have halved maternal mortality levels since 1990 and countries in other regions, including Asia and North Africa have made even greater headway, the global maternal mortality ratio (the number of maternal deaths per 100,000 live births) declined by only 2.3% per year between 1990 and 2015. According to the estimate approximately 303,000 women either died during pregnancy or after childbirth in 2015.

The high number of maternal deaths in some parts of the world is due to the lack of proper access to health services and highlights the gap between rich and poor. Almost all maternal deaths (99%) occur in developing countries with more than half of these deaths in sub-Saharan Africa and almost one third in South Asia. The maternal mortality ratio in developing countries in 2015 is reported to be 239 per 100,000 live births versus 12 per 100,000 live births in developed countries. There are large disparities not only between countries, but also within countries, and between women with high and low income and those women living in rural versus urban areas.

On an average, women in developing countries have more pregnancies than women in developed countries and their lifetime risk of death due to pregnancy is higher. The risk of maternal mortality is highest in adolescent girls under the age of 15 and complications in pregnancy and childbirth is a leading cause of death amongst adolescent girls in developing countries. The lifetime risk of maternal death in a 15-year-old woman in developed countries is 1 in 4900, whereas the same in developing countries is 1 in 180. ("Global, regional, and national levels and trends in maternal mortality between 1990 and 2015, with scenario-based projections to 2030: a systematic analysis by the UN Maternal Mortality Estimation Inter-Agency Group. Alkema L, Chou D, Hogan D, Zhang S, Moller A B, Gemmill A, et al. Lancet. 2016; 387 (10017): 462-74. doi.org/10.1016/S0140-6736(15)00838-7)

Most of the pregnancy and childbirth related complications that lead to death, are either preventable or treatable. Certain pre-pregnancy complications might worsen during pregnancy, especially if not managed as part of the woman's care and some are caused by or associated with diseases such as malaria and AIDS, acquired during pregnancy. While most maternal deaths are preventable, they are still high and increasing given the fact that the health-care solutions to prevent or manage complications are well known.

Therefore, there exists a long felt need for a maternal mortality preventing system that addresses all levels of maternal and infant health and provides personalized treatment strategies.

BRIEF DESCRIPTION OF DRAWINGS

An understanding of the features and innovations of the present disclosure will be realized by reference to the accompanying drawings. The drawings are intended to illustrate, not limit, the present teachings. Various embodiments of the claimed invention incorporating teachings of the present disclosure can be shown and described with respect to the drawings herein, in which:

SUMMARY OF THE INVENTION

Figure 1:
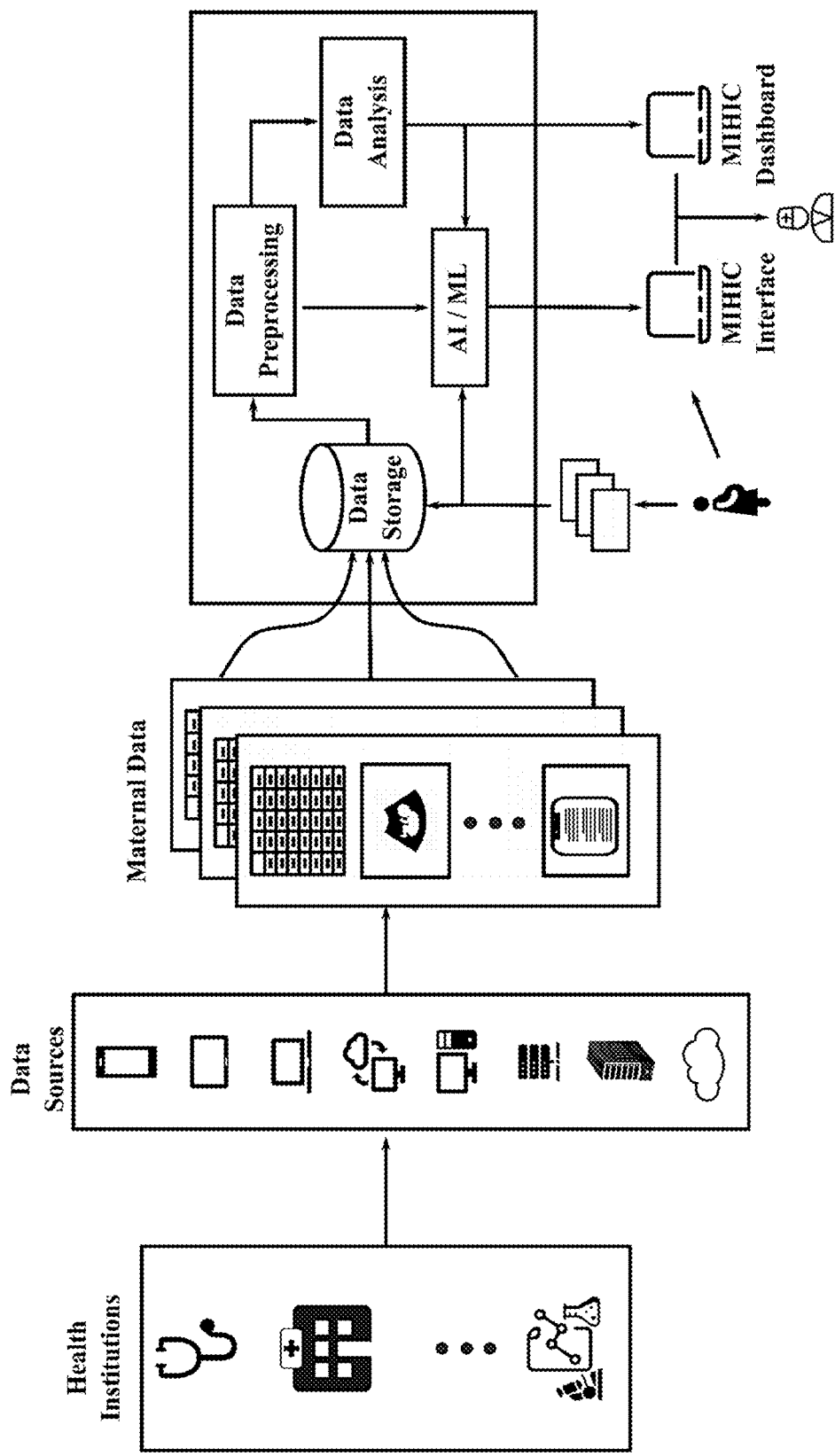
FIG. 1—illustrates the overview of the MIHIC System.

Accordingly, in various embodiments of the claimed invention, the invention herein relates to a Maternal and Infant Health Insights and Cognitive Intelligence (MIHIC) scoring system for predicting and stratifying pregnant mothers into High, Medium and Low risk categories through its MIHIC scores.

The MIHIC system predicts the risks to mother, fetus and infant early enough during the pregnancy, before the risks actually manifest, so as to drive interventions in the patients identified that have a high risk probability. These insights empower the clinicians, caregivers, payers and policymakers to intervene early and pro-actively to manage the risks.

The MIHIC system, in various embodiments as disclosed herein, uses the data related to the available risk factors that cause maternal mortality in women during pregnancy, child birth and post pregnancy. It provides specific risk factors in each individual pregnant woman thereby helping the Clinicians to devise patient specific preventive treatment strategies. The MIHIC system as disclosed herein not only helps the Clinicians to devise patient specific preventive treatment strategies to prevent pregnancy related deaths but also to devise treatment strategies that aid in the delivery of a healthy child. Accordingly, the MIHIC system improves healthcare outcomes in mother, fetus and child by decreasing maternal and infant mortality rates, while improving other indicators of maternal and infant health by enabling early interventions in risky pregnancies.

The MIHIC system helps the Clinicians in providing preventive strategies based on the risks identified and therefore reduces the cost of interventions by targeted interventions in high risk pregnancies as against performing unnecessary interventions in all pregnant women, specifically late interventions. Furthermore, the MIHIC system helps Clinicians in managing Low risk pregnancies in terms of costs and time of the caregivers.

The MIHIC system helps Clinicians detect the risk of maternal mortality in women by understanding and quantifying risk as a single score. MIHIC scores are statistically computed at a patient (a pregnant mother) level by calculating specific scores of the mother, fetus and infant for a defined set of risks and then statistically deriving the overall MIHIC score. The scoring engine takes into account both structured data (including, but not limited to, i.e., biochemistry or bio-markers, socio-economic and demographic) and unstructured data (including, but not limited to, i.e. images, genetics, Clinician notes/images/videos, social media) and applies advanced Artificial Intelligence and Deep Learning methods (including, but not limited to, Neural Networks, Bayesian Networks, Decision Trees, Random Forests, Multi-variate Correlational Analysis etc.) to generate the scores. Clinicians provide their feed-back on actual risks observed and the models learn from those inputs and applied the learning to new MIHIC scoring that can be generated for future patients.

The MIHIC system thus helps to reduce maternal mortality by providing a MIHIC score derived from evidence-based clinical and programmatic evaluation of pregnancy risk factors and thereby helps to provide a more affordable and customized preventive treatment.

The MIHIC system for early detection and assessment of maternal, fetal and infant health risk factors as disclosed herein, comprises of (i) data acquisition modules for acquisition of data from multiple sources in multiple range of digital formats; (ii) data pre-processing modules; (iii) a suite of Artificial Intelligence algorithms to assess the maternal, fetal and infant health risk factors; (iv) a set of interactive dashboards for providing graphical illustrations of indicators and measures of maternal, fetal and infant health; and (v) an interactive web interface, featuring diverse characteristics of pregnant women and to display the statistical measures of risk factors. The MIHIC system provides the statistical measures of the maternal, fetal and infant health risk factors in the form of a MIHIC Score for summarizing the maternal, fetal and infant health status/condition of pregnant women, their fetus and infant.

The data acquisition modules collect data of pregnant women comprising demographics, medical, clinical and genetic data from information systems of clinics, laboratories, pharmacy, health insurances and other government public data sources, by leveraging scraping techniques for extracting data from the multiple sources, and transform them into structured data format before storing in local storage devices.

The data pre-processing modules perform data augmentation for (i) structured data—to reduce data inaccuracy, noise and inconsistency, (ii) unstructured data—to format data conversion, elimination of stop words/punctuations/non-ascii characters, identification of stem words and lemmatization, and (iii) images.—for better data image representation.

The suite of AI algorithms comprise a set of machine learning models/techniques trained to learn to extract information/data from the structured and unstructured data, assemble knowledge from the extracted data and map the assembled data to the characteristics of associated maternal, fetal and infant risks to perform a risk prediction, wherein the machine learning models are selected from, but not limited to, logistic regression, Support Vector Machine (SVM) regression and neural networks which include but not limited to, convolutional neural network (CNN), recurrent neural network (RNN) and long short-term memory model (LSTM).

The interactive dashboard comprises of (i) Graphical depiction of indicators about pregnant women's maternal, fetal and infant health conditions, (ii) Graphical illustration of prevalence of risk factors associated with a risk of interest across different population groups, (iii) Charts showing associations and correlations between risk factors affecting Maternal health of pregnant women across different population groups, and/or (iv) Charts showing associations and correlations between risk factors affecting Infant health across different population groups.

The interactive web interface comprises of (i) an input platform for input of data by Clinicians and pregnant women and (ii) a display platform for providing the insights regarding the maternal health condition rendered as risk scores in a webpage and (iii) a display platform for providing the insights regarding the maternal health condition rendered as graphical charts on the interactive dashboard using various risk indicators of pregnant women.

Also disclosed herein, is a method of detecting and assessing insights for maternal, fetal and infant health risk factors using a maternal and infant health insights and cognitive intelligence (MIHIC) scoring system comprising (i) acquiring/capturing demographic, medical, image, clinical and genetic data/characteristics of pregnant woman from multiple sources; (ii) identifying data formats of the acquired/captured data and segregating the data into structured and unstructured data; (iii) pre-processing and cleaning the structured, unstructured and image data and assembling the pre-processed data; (iv) forwarding the pre-processed/cleaned data to the AI suite for exploration of factors associated with risks; (v) computing MIHIC scores for various types of risks and risk indicators; and (vi) providing the MIHIC risk score and insights to understanding behavior of risk factors for cohorts as graphical presentations through a dash board.

DETAILED DESCRIPTION OF THE INVENTION

The MIHIC system comprises an algorithm and a method to determine a risk score between 0 and 1 (derived by applying an algorithm to process probabilities of risk). The MIHIC system uses self-learning models including, but not limited to, reinforcement learning to continually improve the prediction of score and stratification of risk level as Low, Medium and High. MIHIC score is a quantification of identified possible risks to the mother, fetus and infant. The score uses a specialized algorithm to derive the individual and overall risk as a value between 0 and 1.

MIHIC system as disclosed herein determines the propensity for maternal, fetal and infant risk based on a score predicted given the medical, clinical and biological characteristics of pregnant women. Computing such an individual risk score for each pregnant mother for maternal, fetal and infant risk can aid the Clinicians/Care-givers in clinical decision making for assessment of maternal health and timely intervention to prevent pregnancy related complications. The MIHIC ecosystem has various components with a suite of Artificial Intelligence algorithms developed using software such as Python and R. FIG. 1 includes the overview of the MIHIC system in various embodiments of the claimed invention. Designing and developing such a complex computation system for predicting risks utilizes a software ecosystem/platform with robust computational infrastructure encompassing components for:

Gathering data from multiple sources—Nurses, Doctors, Clinicians, Labs, Hospitals etc.;
Using diverse technologies for collection, processing, storage and distribution of data such as Smart Phones, iPads, Desktop/Personal Computers, Stand-alone/On-Premise/Cloud Servers etc.;
Organizing data in a main storage and in auxiliary storage devices;
Data preprocessing analytics; Cleansing of data stored in databases is known to improve performance of subsequent processes (analytics and prediction) in the pipeline;
Dashboard for rendering insights from analytics;
A suite of Artificial Intelligence {AI} and Machine Learning {ML} algorithms for learning knowledge to predict risks; and
Web interface that displays maternal health given the characteristics of pregnant women using the knowledge from AI algorithms.

Input—Data Acquisition

MIHIC system acquires data from multiple sources as the patient/pregnant woman's characteristics are captured and stored by different entities at various places, multiple times. In general, pregnant women's characteristics are categorized under demographic, medical, clinical and genetic. Some of the pregnant women's characteristics used in the MIHIC system for gaining insights into maternal and infant risks are:

Demographic: Age, Parity, Race, Socioeconomic status, Home Owner, Occupation, Lifestyle, County, Social Network;
Medical: Gestational Weeks BMI, Family Medical History, Trimester, Blood Pressure (mmHg), Diabetes mellitus, Haemoglobin (g/dL), Foetal Heartrate (bpm), Symptoms, Diagnosis;
Clinical: Urine Protein (mg/24 hour), Protein/Creatinine ratio, Serum creatinine (mg/dL), Serum uric acid (mg/dL), Indirect bilirubin (mg/dL), Lactate Dehydrogenase LDH (U/L), Platelet count (/mm3), Fibrinogen (g/L), Glucose Plasma (mg/dL), Prothrombin time-plasma (seconds);
Genetic: Biomarker VEGF (Vasclular Endothelial Growth Factor), PlGF (Placental Growth Factor), sFit-1 (soluble fms-like tyrosine kinase 1), Seng (Soluble endoglin).

Each of these characteristics are captured in different data formats. Some of these characteristics are stored in a structured format/represented tabularly. However, information about laboratory tests and results are represented as reports while Clinicians' notes are often textual, audio, video files. Furthermore, all of the patients' medical scans are in image format. Some of the clinical characteristic can be captured and stored in a data format such as CSV/Excel/JSON/XML/PDF/TXT, but ultrasound scans are stored in unstructured image format. Further, summarization of textual data from laboratory reports and clinical notes can be performed by applying pre-processing techniques.

The MIHIC system leverages a suite of Machine/Deep Learning algorithms for exploration of factors associated with risk and subsequently computes the scores for various types of risks. The system adopts and stacks numerous techniques for performing the tasks such as pre-processing, exploratory analysis and prediction of risk score.

Figure 2:
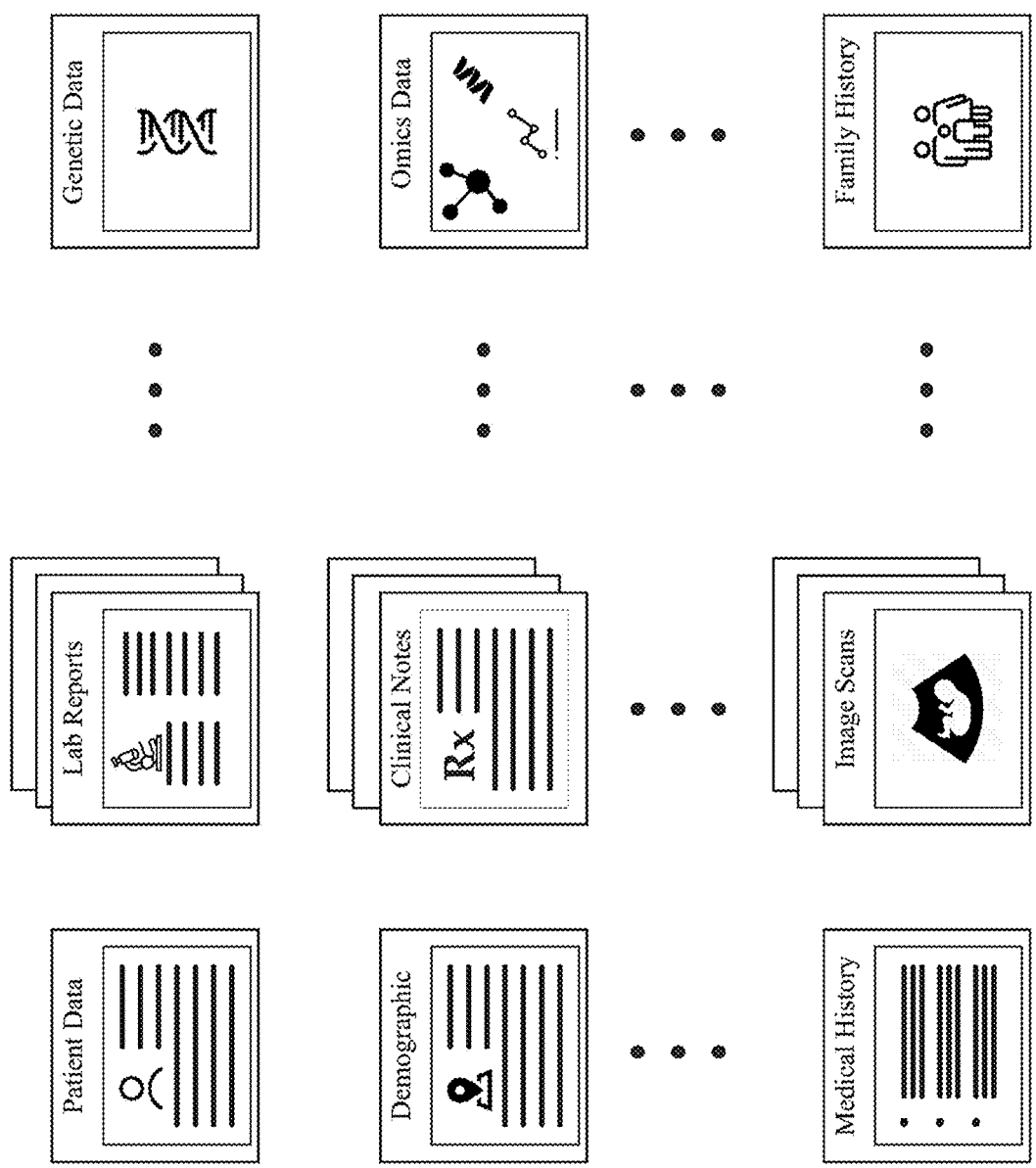
FIG. 2—illustrates the different Types of Input Data.

Usually, the characteristics of the mother are obtained from multiple sources and as illustrated in FIG. 2, the data formats vary between sources depending upon how the data is stored and organized. Medical data is well known to be inaccurate, noisy and inconsistent due to the nature of data acquisition process and diversity of the nature of data.

Therefore, the MIHIC system runs its pre-processing algorithms that deal with processing both structured and unstructured data. These algorithms pre-process the structured, unstructured and image data and then forward the cleaned data to the subsequent modules for further processing and analysis. Some of the challenges in cleaning medical data and pre-processing approaches are:

Structured Data

Data Inaccuracy—handling the incomplete, missing values can be done using traditional techniques such as imputation with mean, normal values and also with model-based approaches such as multivariate regression and k-nearest neighbor.

Data Noise—reducing noise by removing erroneous data and outliers from the data by multivariate approaches using different similarity measures such as Mahalanobis and Cook.

Data Inconsistency—identified when data is input from various sources. During this time the source with the most inconsistent data can be identified and can be addressed using correlation analysis.

Unstructured Data

Dr. Notes/Text: For textual data the normalization can be a task for analysis of clinical notes and patient's laboratory reports. With normalization, MIHIC system handles some of the challenges in text processing such as:

Format/Code Conversion—data from multiple sources in various formats/codes can be collected and converted to simple format. MIHIC system incorporates Scripts for converting files in different formats to one standard format.

Eliminating Stop Words/Punctuations/Non-ASCII characters—MIHIC system incorporates regular expression scripts to eliminate the stop words, punctuations and non-ascii characters.

Identifying Stem Words—reducing each word in the text to base or root will improve the analysis of textual data. MIHIC system comprises modules for performing stemming on clinical and laboratory notes.

Lemmatization—as used herein can refer to reducing words to base form by considering the context along with the content is known as lemmatization and can be useful in identifying clinical, biological entities in notes or reports. Alternatively, lemmatization of words helps to tag the text.

Medical Scans/Images

For processing medical images, the MIHIC system can provide modules to perform the following tasks:

Image Resize & Normalization—Images of different patients collected from different sources usually have different dimensions that are to be resized. According to various embodiments the MIHIC system encompasses methods such as nearest neighbor and neural networks to perform up-scaling and down-scaling of images and also methods for transformation.

Noise Reduction—Noise in the medical images occurs due to variation in capturing and can be undesirable for image analysis. Therefore, the MIHIC system comprises techniques that supports reduction of various types of noises including, but not limited to, Pepper, Gaussian and Poisson. According to various embodiments the MIHIC system comprises Neural networks-based modules to suppress the noise in scanned images.

Blur—Along with noise the other major distorter for quality of an image is blur and results in affecting the accuracy of the prediction models. According to one embodiment the MIHIC system comprises Kernel filters such as gaussian blur, deep neural networks, to sharpen and blur the images during the training of the prediction model. Consequently, during real time prediction the model would have acquired resistance to blurring in the medical images.

EDA—Exploratory Data Analysis: MIHIC system also considers the synthesized results pertaining to the factors associated with maternal, fetal and infant risks. These results can show the incidence and prevalence of the factors for risks besides providing deep insights into understanding the behavior of risk factors for different cohorts. Such an exploratory analysis can be used by Clinicians in designing the prevention and intervention strategies. Results can be rendered by rich graphical presentations through a dashboard that enables easy interpretation and assessment of risk indicators. Some of the visualizations rendered in the dashboard include, but are not limited to:

Visualization of indicators such as maternal mortality rate, infant mortality rate, spread of maternal mortality by geographical area etc. are usually depicted using the charts speedometer, gauge meter and horizontal bar charts.

Figure 6:
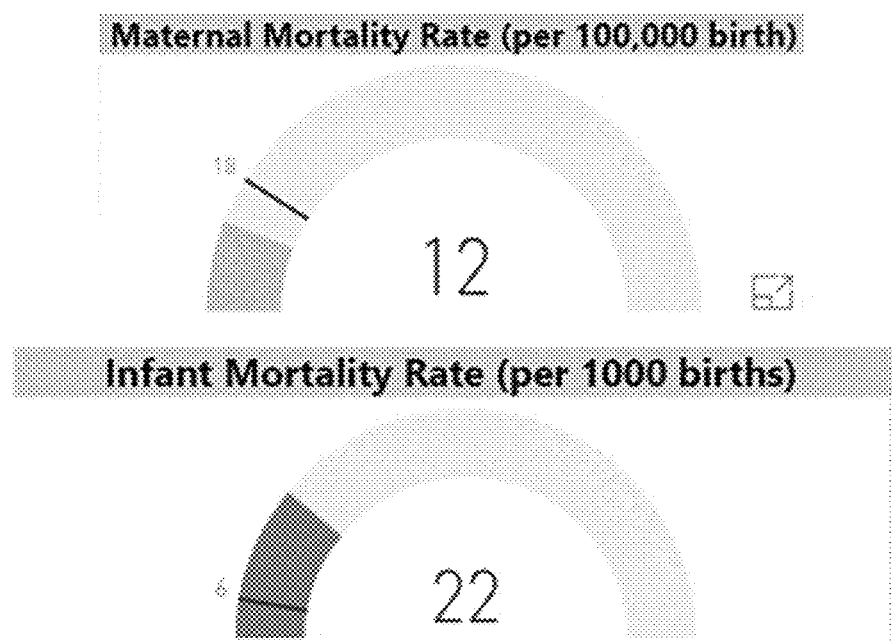
FIG. 6—is a graphical representation of the maternal and infant mortality rate which depicts there were 12 maternal deaths per 100,000 births and 22 infant deaths per 1000 births.
Figure 7:
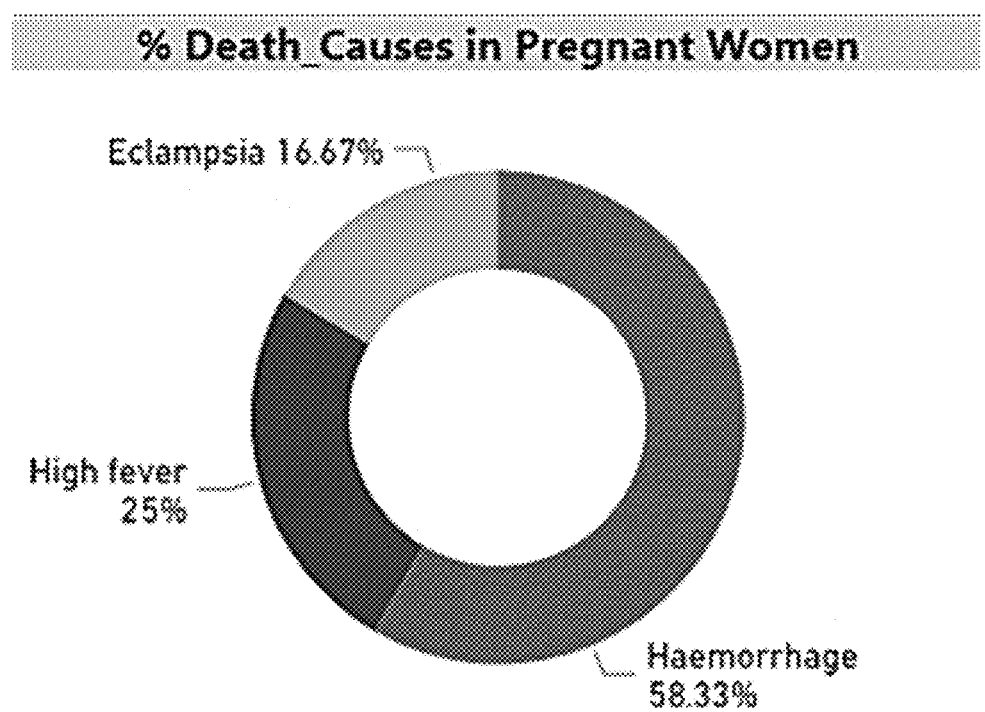
FIG. 7—is a graphical representation of distribution of pregnant women by causes of death which were Eclampsia (16.67%), High Fever (25%) and Hemorrhage (58.33%).
Figure 8:
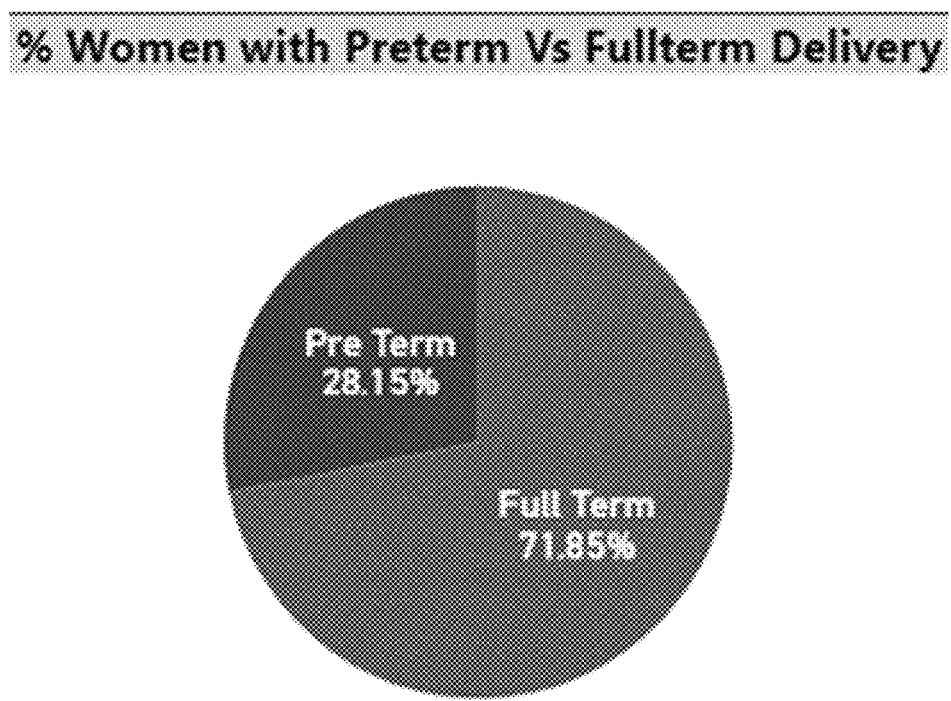
FIG. 8—is a graphical representation of type of infant deliveries which were preterm (28.15%) and full term (71.85%) expressed as a percentage for a sample size of 1000 simulated records.

FIG. 6 graphically illustrates maternal and infant mortality rates. For example, the interactive dashboard has speedometers depicting number of maternal deaths per 100,000 births and number of infant deaths per 1000 births. FIG. 7 graphically illustrates causes of death in pregnant women. Exemplary causes of death depicted using a donut chart are eclampsia, high fever and hemorrhage. FIG. 8 graphically illustrates types of delivery in pregnant women as percentage of preterm and full-term deliveries using a pie chart.

Prevalence of certain risk factors by demographic characteristic of patients can be illustrated using distribution charts, boxplots, violin plots, pie and bar charts.

Figure 9:
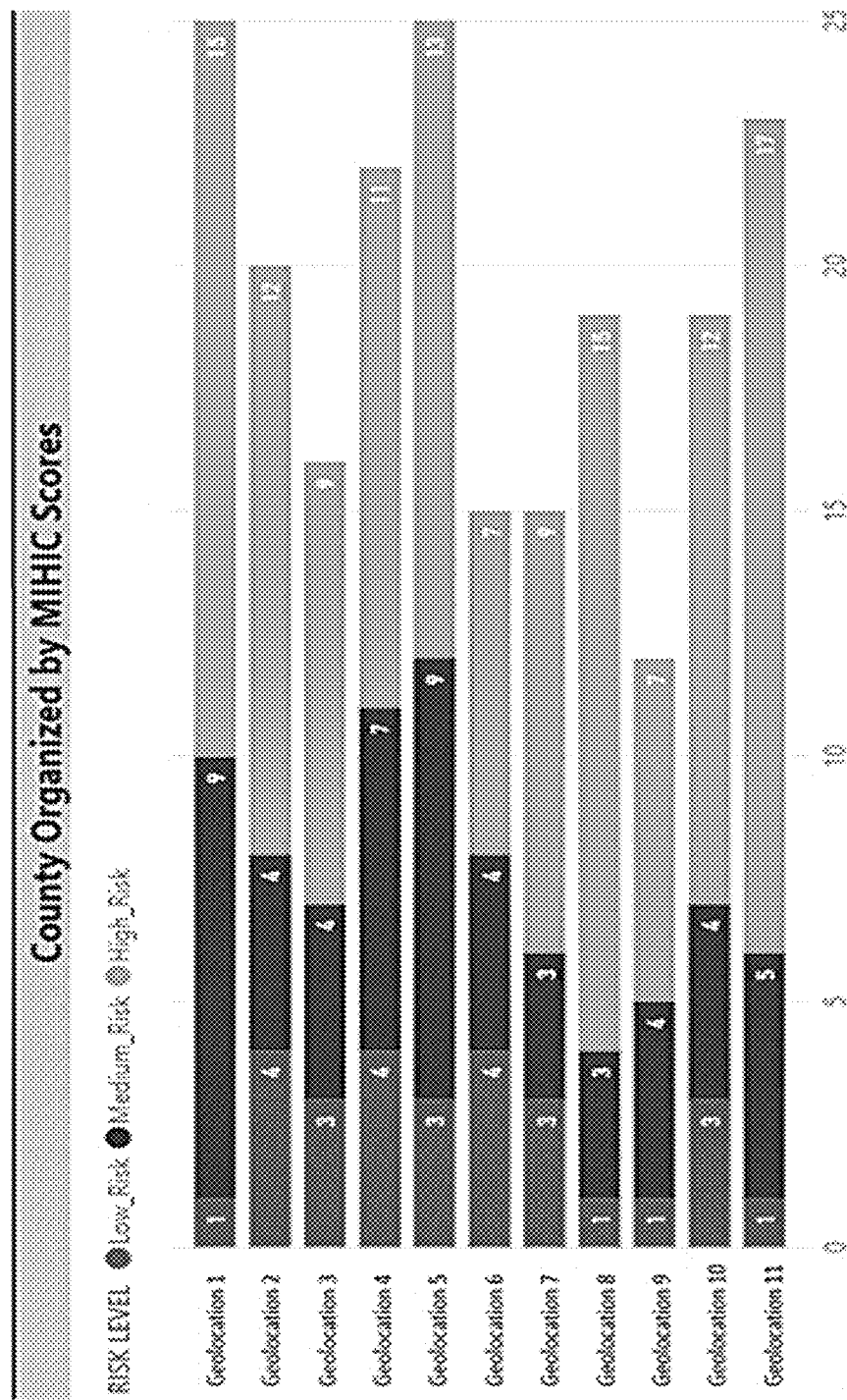
FIG. 9—is a graphical representation of number of pregnant women across different geolocations by MIHIC risk level.
Figure 10:
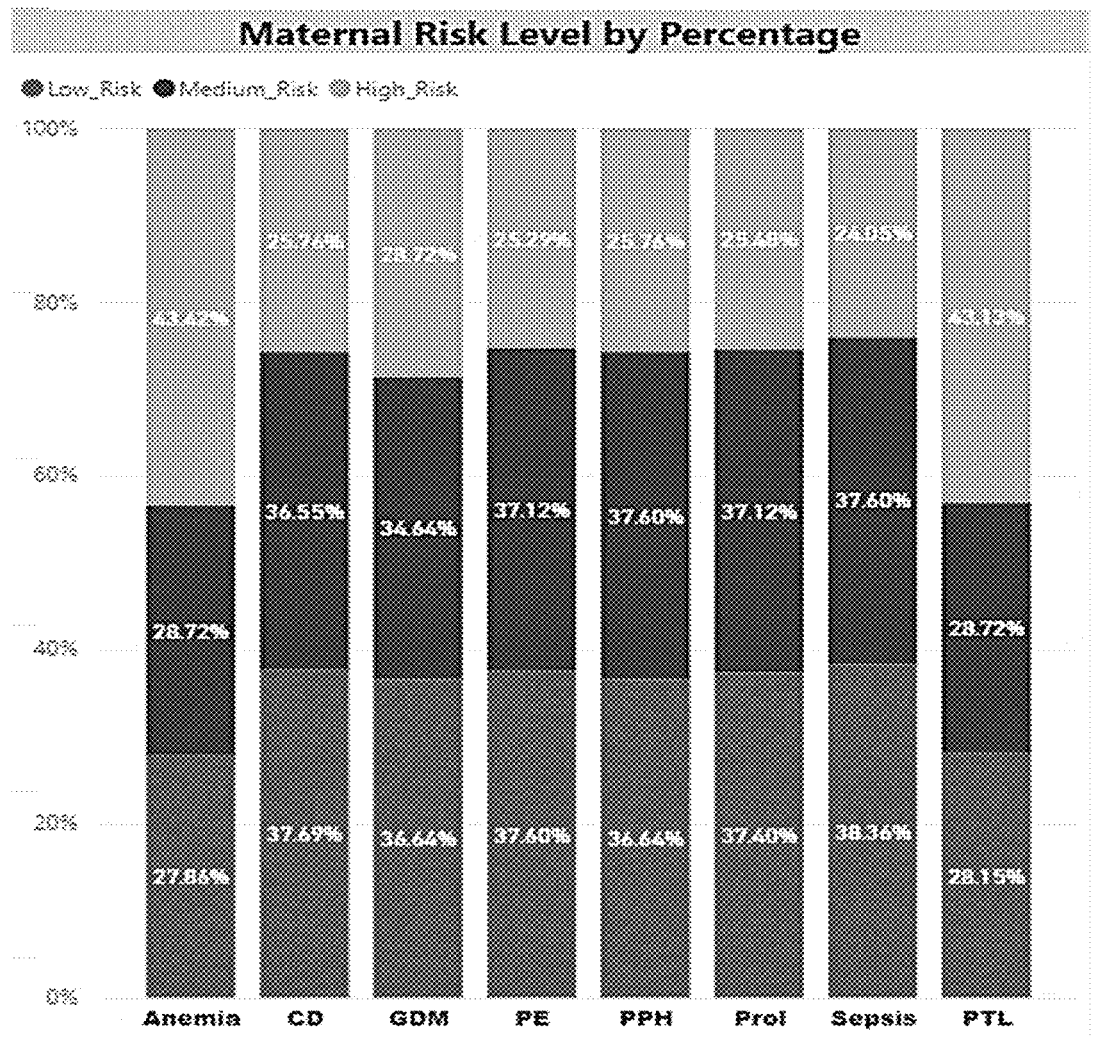
FIG. 10—is a graphical representation of % age of pregnant women across different pregnancy risks by MIHIC Risk Levels.

FIG. 9 illustrates MIHIC scores of pregnant women in 11 sub-locations within a demarcated geographical region. Listed are the number of pregnant women having propensity for low, medium and high-risk levels for maternal and infant risk within each of the 11 geographical sub-locations. The data supports the hypothesis that proximity to quality healthcare within a geographical region may be insufficient to result in receipt of adequate healthcare as evidenced by the stark differences in the number of high risk pregnancies compared to combined numbers of low and medium risk pregnancies in a given sub-location. For example, a comparison of Geolocation 8 vs. Geolocation 4 indicates that 79% (15/19) of the pregnancies were high risk in Geolocation 8 but only 50% (11/22) were high risk pregnancies in Geolocation 4. FIG. 10 illustrates the percentage of women having risk for the listed pregnancy complications considered for maternal and infant risks. For example, the stacked column chart depicts percentage of women having propensity to a low, medium and high levels of risks to the complications of anemia, congenital disease (CD), gestational diabetes (GDM), preeclampsia (PE), postpartum hemorrhage (PPH), prolonged labour (ProL), sepsis and preterm labour (PTL).

Association between risk factors and clinical characteristics can be illustrated using scatter plots, correlation matrices depicting the degree of association and their impact on the maternal and infant risks.

Comparison charts such as column, bar and line charts help in understanding behavior of different cohorts of interest with each other and also within the population with respect to the factors of interest.

Figure 11:
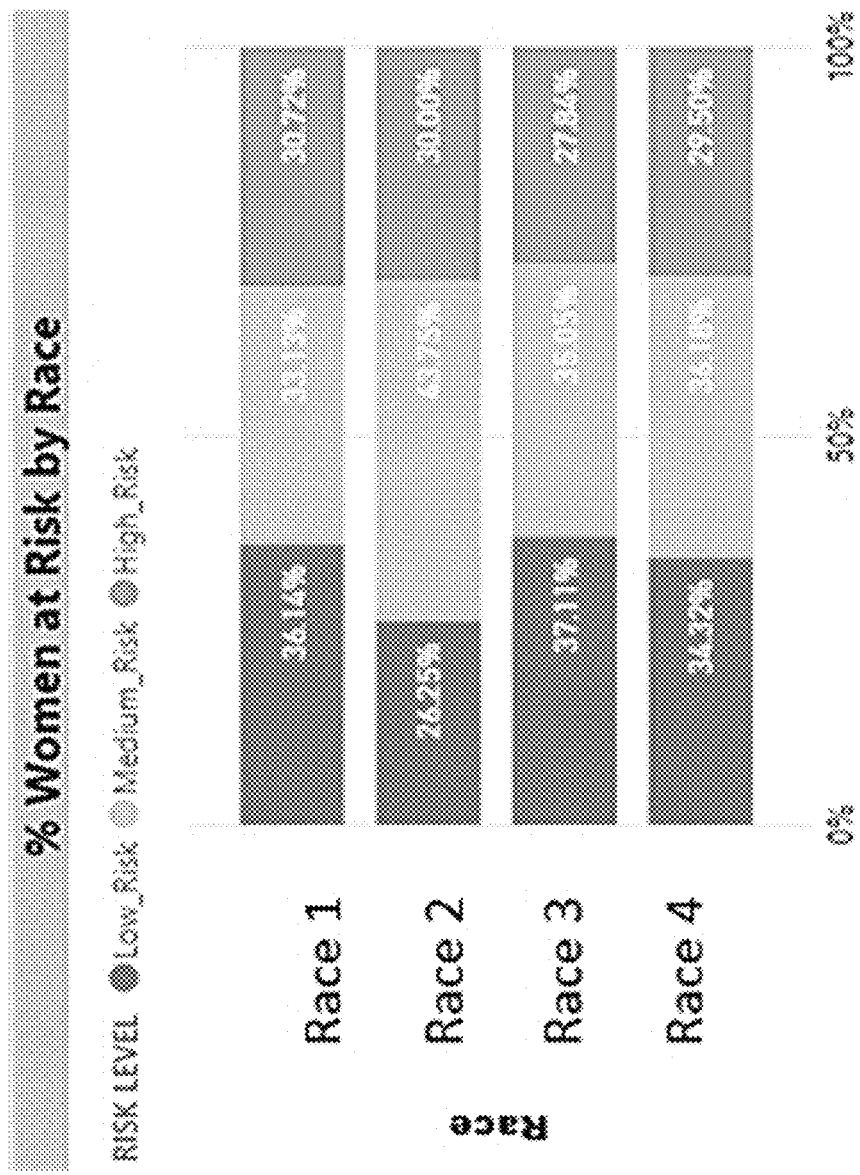
FIG. 11—is a graphical representation of % age of pregnant women across races with different risk levels for Preeclampsia.
Figure 12:
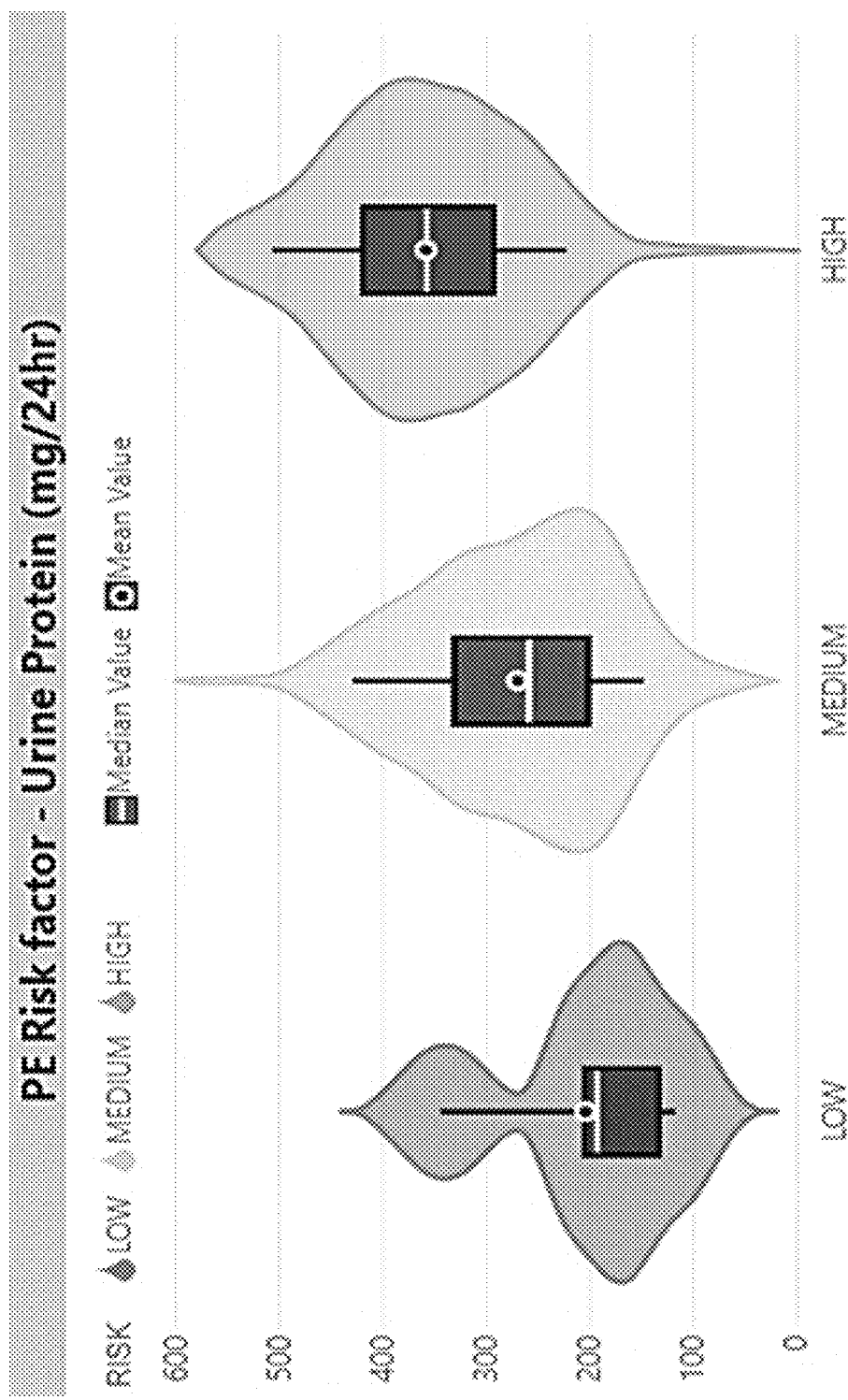
FIG. 12—is a graphical representation of association of Preeclampsia with risk factor urine protein.
Figure 13:
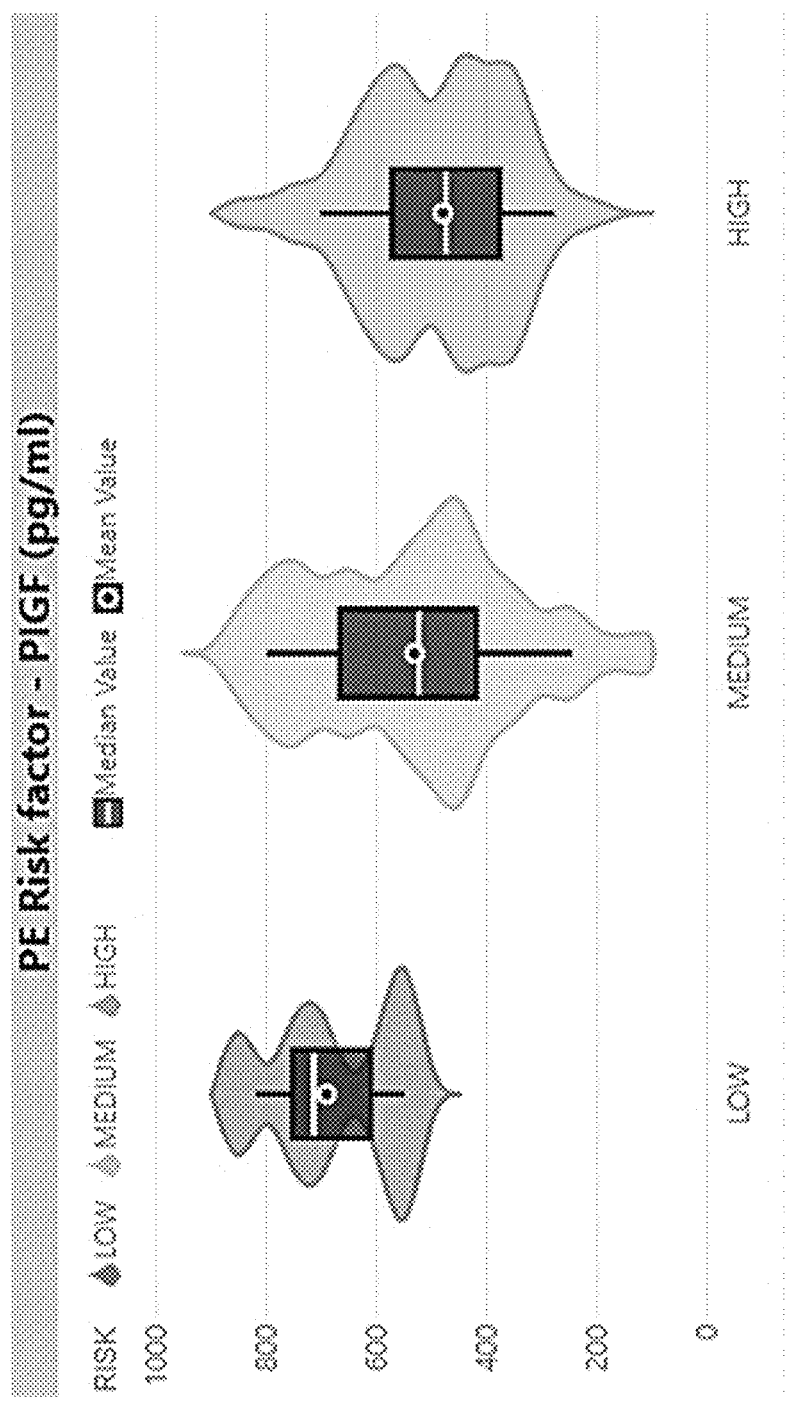
FIG. 13—is a graphical representation of association of Preeclampsia with biomarker Placenta Growth Factors (PIGF).
Figure 14:
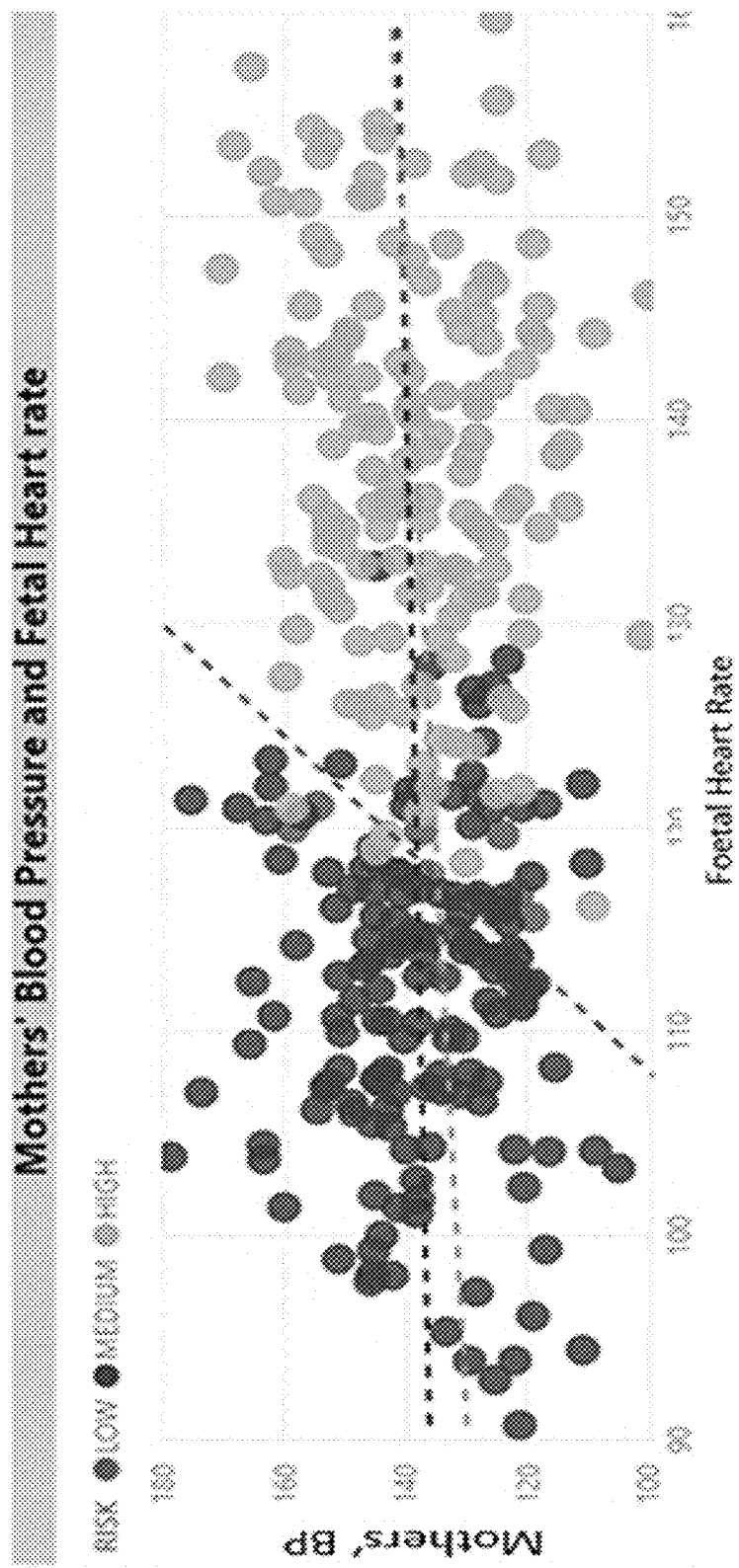
FIG. 14—is a graphical representation of association between Mothers' Blood Pressure and foetal heart rate with preeclampsia risk levels.
Figure 15:
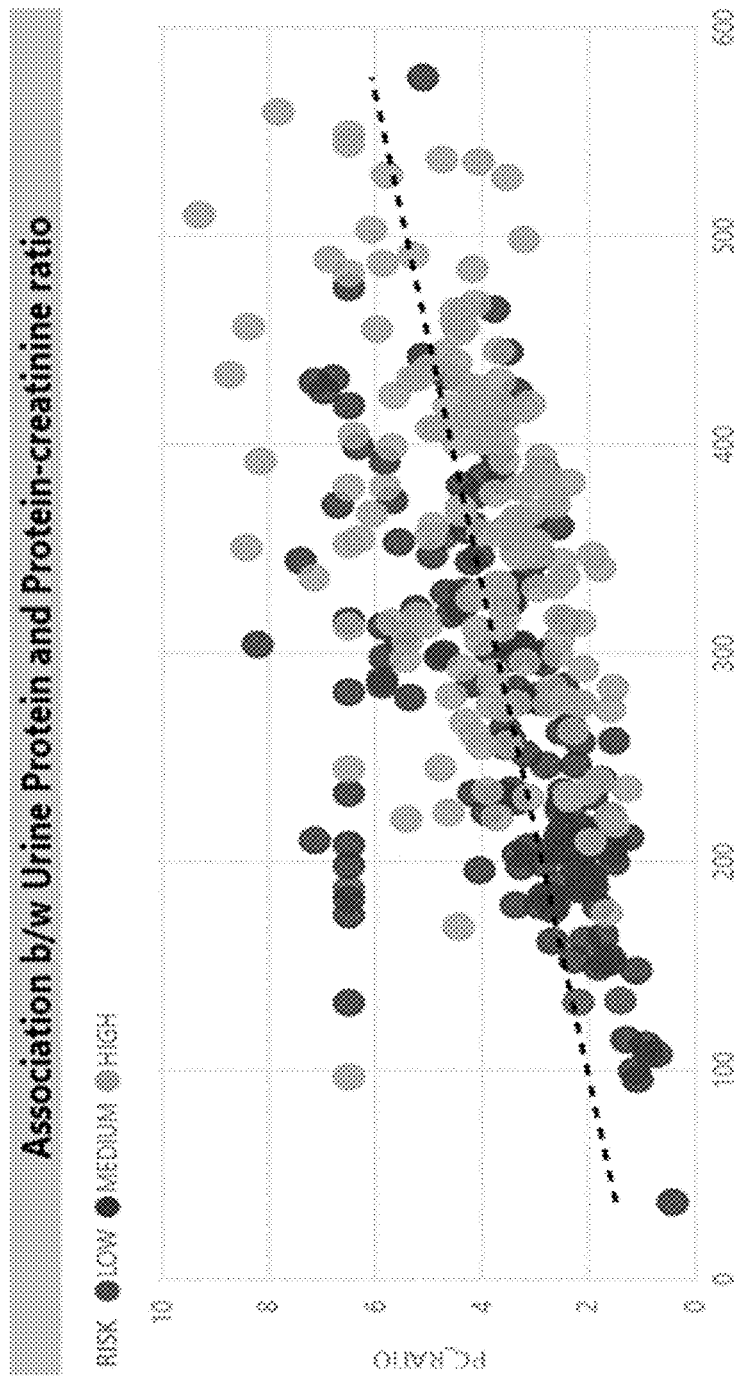
FIG. 15—is a graphical representation of Urine Protein and Protein-Creatinine ratio vs. Preeclampsia risk levels.

FIG. 11 is a graphical illustration of percentage of women at risk by Race. A stacked bar chart is utilized to depict risk levels of four races—Race 1, Race 2, Race 3 and Race 4. All the pregnant women from four races have propensity of high maternal risk; However, data analysis reveals that women belonging to Race 2 are more prone to maternal risks than women from other races. FIG. 12 illustrates association of risk factor "urine protein" with the different risk levels of "maternal preeclampsia (PE)", depicted using violin charts. It conveys that women with high risk for PE have Urine protein values distributed across the mean with 360 mg/24 hr and have minimum and maximum values around 290 mg/24 hr and 420 mg/24 hr, respectively. Urine protein values of the women who are at medium and low risks for PE are with mean 260 mg/24 hr and 200 mg/24 hr, respectively. FIG. 13 depicts association of Placental growth factor (PIGF) with the different risk levels of maternal preeclampsia (PE). Violin charts depicted provide an understanding for the distribution of PIGF values across different risks levels of PE. From the chart it can be interpreted that PIGF values decline with increase in the risk for PE. Among the women having high risk for PE, PIGF values are centered around 500 pg/ml, while mean for medium and low risk populations are centered around 620 pg/ml and 710 pg/ml, respectively. FIG. 14 includes the graphical illustration of association of mother's blood pressure and foetal heart rate across mothers having different risk levels of preeclampsia depicted in a scatter plot. Their strength of the relationship can be assessed thus: in the women having low risk for PE, the relationship between the blood pressure and heart rate is linear and strongly correlated. But in case of other groups the medium and high risk relationship is not linear and has high numbers of outliers. FIG. 15 depicts a scatter plot representing the association of Urine protein and protein creatinine ratio (PCR) across mothers having different risk levels of preeclampsia. The chart shows type of correlation and strength of relationship for the two preeclampsia risk factors. For example, in the women having high risk for preeclampsia the relationship between Urine protein and PCR is linear, with strong positive correlation. There are a moderate number of outliers present in this relationship. Furthermore, in women with medium risk for preeclampsia, the plot shows very strong linear association with a smaller number of outliers. Relationship between the two risk factors for women having low risk for preeclampsia is weak, with relationship being non-linear and with a high number of outliers.

Figure 16:
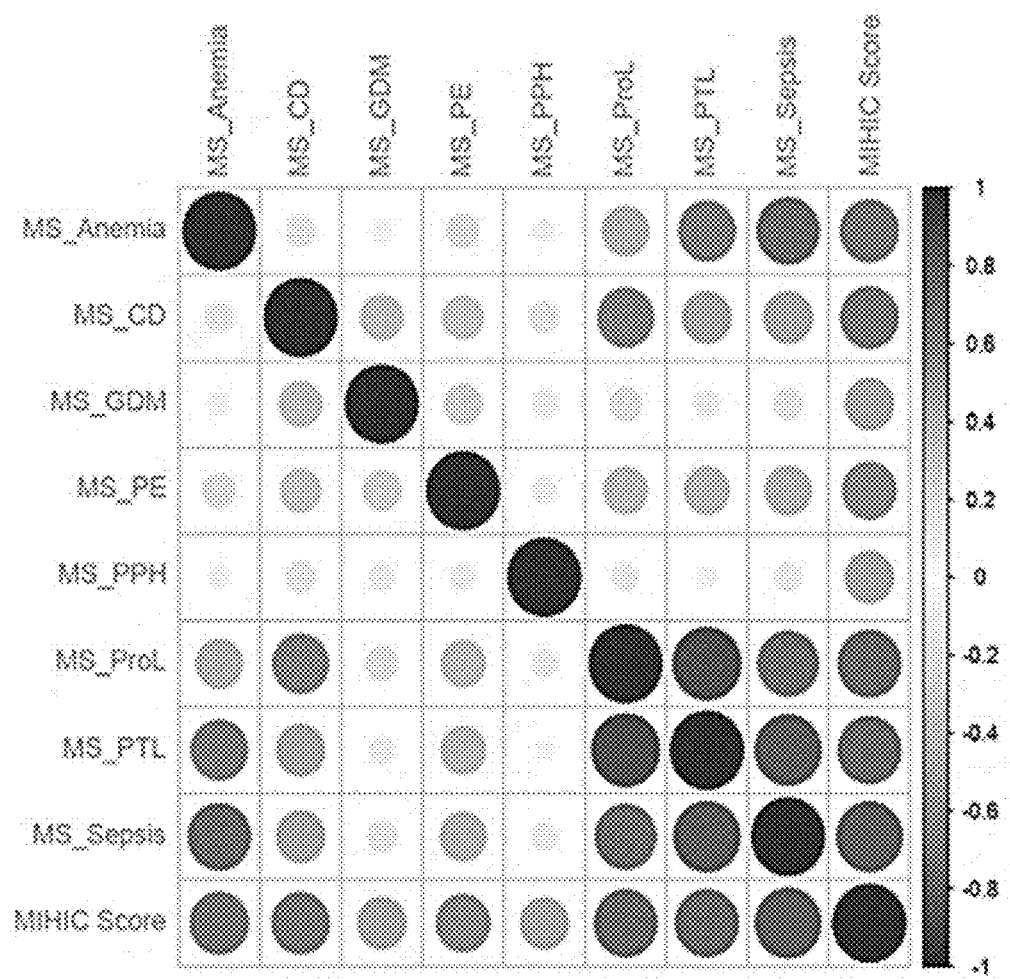
FIG. 16—is a graphical representation of correlation between various pregnancy risks and MIHIC score.

FIG. 16 includes a graphical illustration showing the association of two pregnancy complication risk scores for accessing maternal risk. For example, the correlation plot shows how the scores of a risk can be associated with another risk considered. Complications compared were anemia, congenital disease (CD), gestational diabetes (GDM), preeclampsia (PE), postpartum haemorrhage (PPH), prolonged labour, sepsis and preterm labour (PTL).

Artificial Intelligence for Prediction: In various embodiments of the claimed invention, the MIHIC system as disclosed herein strives to predict the likelihood of maternal, fetal and infant risks. For predicting each risk, the system employs a suite of Artificial intelligence techniques to determine a risk score with values between 0 and 1. These techniques can be trained on millions of medical records having medical, clinical and biological characteristics of the mothers to attain the ability to generalize maternal and infant risks. Pre-processed data can be forwarded to the AI Suite for learning how to generalize and predict. The Suite can have a set of machine learning techniques that learn how to preprocess the data, extract information from the texts and images and subsequently assemble the knowledge to perform risk prediction.

Representation Learning: Performance of the prediction model depends upon the quality of data pooled for training the model. Deep neural network models are trained to learn data representation for the data considered as the input. To improve the performance of the prediction model, vector representation can be adopted to denote the content in the medical records. Furthermore, information extracted from clinical notes and ultrasound scans are also combined with the other characteristics of the data and are represented as vectors.

Learning & Extracting from Text Data: The AI suite of the MIHIC system has neural network models of type recurrent neural networks to perform the task of extracting information from the unstructured data such as lab reports, Clinician's notes etc. Model can be trained to identify the clinical concepts in text and map them to the standard clinical approaches. Thereby trained model enables transformation of unstructured text to information represented in vectors.

Learning & Extracting from Image Data: The AI suite of the MIHIC system comprises deep neural network models of type convolutional neural networks to perform the extraction of information from different types of scans such as ultra sound, MRI etc. Networks are trained to learn object segmentation from the scanned images. Once trained, the model has the ability to detect objects from the knowledge it has gained about image features. Upon extraction of the object from the scanned image, information about the properties of the object are represented in vectors.

Learning to Predict the MIHIC Score

Information extracted from the above deep neural networks can then be passed to the stacked neural networks with deep hidden layers. These layers have large number of nodes with non-linear activation functions and thus have the ability to capture the non-linear association with the various data characteristics of the mother. Projection of mother's characteristics to the higher dimension will enhance the opportunity to better understand the association between different characteristics. Training of the model is done in the context of supervised learning. Consequently, the model's ability to identify and extract patterns from the mother's characteristics pertaining to a maternal risk can be reliable with statistical significance. Further, training of the entire stacked deep network can be repeated to identify optimal values of epochs and batch size.

Techniques such as dropout and regularization can be utilized to reduce the bias in the model's prediction and increase its capability to generalize knowledge from the various characteristics to predict a risk. Further, the model's hyper parameters such as depth of the network, dimensions, learning rate and momentum can be fine-tuned to improve their power of predictability of risk by leveraging the optimization techniques including, but not limited to, gradient descent, stochastic gradient descent and their flavors.

Each model in the MIHIC system computes a risk score for maternal, fetal and infant risks considered, to provide a naive measure that comprehensively summarizes the maternal health in the form of MIHIC score. The MIHIC system, in various embodiments of the claimed invention can, then compute the MIHIC score using statistical techniques that derive the score from each of the above models.

Risk Stratification and Insight Delivery: To increase the viability of score interpretation, the prediction results can be stratified into Low, Medium and High. This is done by the MIHIC system by employing modules of statistical techniques to perform operations such as normalization, standardization of predicted values and identification of thresholds to classify a risk score as low, medium and high. Such a classification of risk score, in various embodiments of the claimed invention, can help in easy assessment and interpretation of maternal health of a pregnant woman by all the stake holders of the health care system.

Feed-back layer: In addition, the MIHIC system also provides its algorithms the self-learning capabilities to learn continuously from the data provided. Such an ability in various embodiments of the claimed invention can be potentially useful in identifying and designing optimal intervention/treatment strategies.

The MIHIC Algorithm

The output of the individual risk models gives the probability of a particular risk for e.g. Miscarriage occurring in an individual patient based on the patient's data.

To convert probability to MIHIC score, we used the following algorithm:
max=highest probability for patient in training data set
min=least probability for patient in training data set MIHIC score for individual risk=(probability of risk for the patient−min)/(max−min)

To get MIHIC risk level, we used the following algorithm:
Count number of patients with that risk in the training data set E.g. if 400 patients in training data set have anemia, then 400 highest MIHIC scores should be assigned high risk.

Assign equal numbers to Remaining 2 risk level: medium and low.

This gives the cut off MIHIC scores between high-medium risk and medium-low risk which can be used to stratify new patients into the risk levels. As more data becomes available, these cut off points will change as the algorithm learns from the training data.

The MIHIC system calculates the overall MIHIC score by:
1. Computing the average of all model probabilities per patient in the training data set,
2. Determining the min, max probability and using it to get overall MIHIC score as follows—
   a. Overall MIHIC risk score=(average probability of all risks for the patient−min)/(max−min)
   b. Overall MIHIC risk level—low, medium, and high stratification can be determined similar to the individual MIHIC risk levels shown above. That is, highest 30% of the overall MIHIC scores are categorized as High risk, the next 35% scores are categorized as Medium risk and the lowest scores 35% are categorized as Low risk.

The MIHIC system takes into account each data parameter for the maternal, fetal and infant/neonatal risks to compute the overall MIHIC score. It quantifies the entirety of maternal, fetal and infant/neonatal risks into a single value for stratification of the overall maternal risk and allows early intervention in high risk pregnant women for all common maternal, fetal and infant/neonatal risks. Further, the MIHIC system provides a specific and unique way to predict the maternal, fetal and infant/neonatal risks in pregnant mothers as well as mothers who are planning to conceive pregnancy. It includes a gamut of 48 comprehensive risks covering mother, fetus and infant and can be expanded further.

Mathematical Models Used in the MIHIC Algorithm

Figure 5:
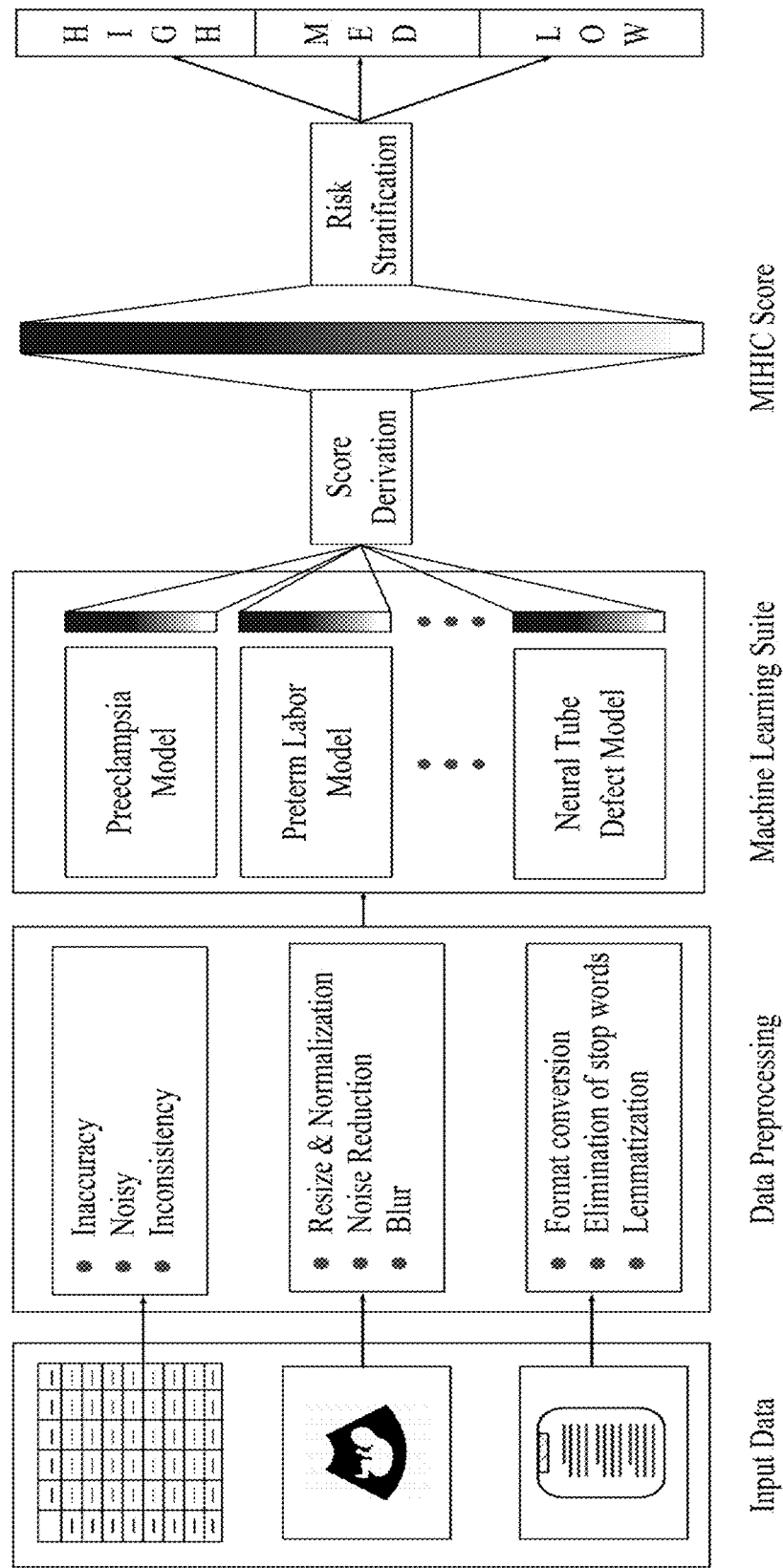
FIG. 5—illustrates the MIHIC Platform.

Given a dataset having characteristics of the pregnant women along with outcomes of delivery, the MIHIC platform processes the data for augmentation and forwards it to the AI suite consisting of various models to gain knowledge by assessing the maternal, fetal and infant conditions. Consequently, the platform formulates a machine learning problem out of the maternal health assessment that the AI Suite processes for insights. FIG. 5 illustrates the MIHIC system for obtaining the MIHIC risk score.

All the medical, clinical, historical and other data captured during the pregnancy period is considered as input X to the model and outcome of the delivery denoted by Y is considered as output. Here the outcome can be any of the possible maternal, fetal and infant risks. The outcome Y, has multiple real values between 0 and 1 represented as $y_i$. Each $y_i \in Y$ represents propensity for a risk.

TABLE 1

90 Characteristics considered for computation of MIHIC score for maternal health assessment.

1 Abortion
2 Age of Pregnant Women
3 Age of Last child born
4 Anaemia
5 Biomarker: VEGF
6 Biomarker: PlGF
7 Biomarker: sEng
8 Biomarker: sFit-1
9 Birth Defects
10 Birth Weight
11 Cancer
12 Chickenpox
13 Complaints
14 Date of Conception
15 Delivery Outcomes
16 Delivery Place
17 Diabetes Mellitus
18 Diarrhoea
19 Diastolic Blood Pressure
20 Expected Date of Delivery
21 Eye problem
22 Family economic status
23 Fasting Blood Sugar
24 Fibrinogen (g/L)
25 Fetal heart Rate
26 Fetal Movement
27 Fetal Presentation
28 Full-term Delivery
29 Fundal Height
30 Gender of Last child born
31 Gestational Age
32 Gestational Diabetes
33 Glucose Plasma (mg/dL)
34 Haemoglobin
35 Health Status during Delivery
36 Height of Pregnant Women
37 High Risk Symptoms/Complaints
38 HIV
39 HIV Status
40 Hypertension
41 Indirect bilirubin (mg/dL)
42 Infant Mortality Rate
43 Jaundice
44 LDH (U/L)
45 Leprosy
46 Maternal Mortality Rate
47 Measles
48 Medical History
49 Maternal Death
50 Mental Disorder
51 Non communicable disease diagnosis
52 Number of Folic Acid Tablets Given
53 Number of IFA Tablets Given
54 Obesity

TABLE 1-continued

90 Characteristics considered for computation of MIHIC score for maternal health assessment.

Figure 3:
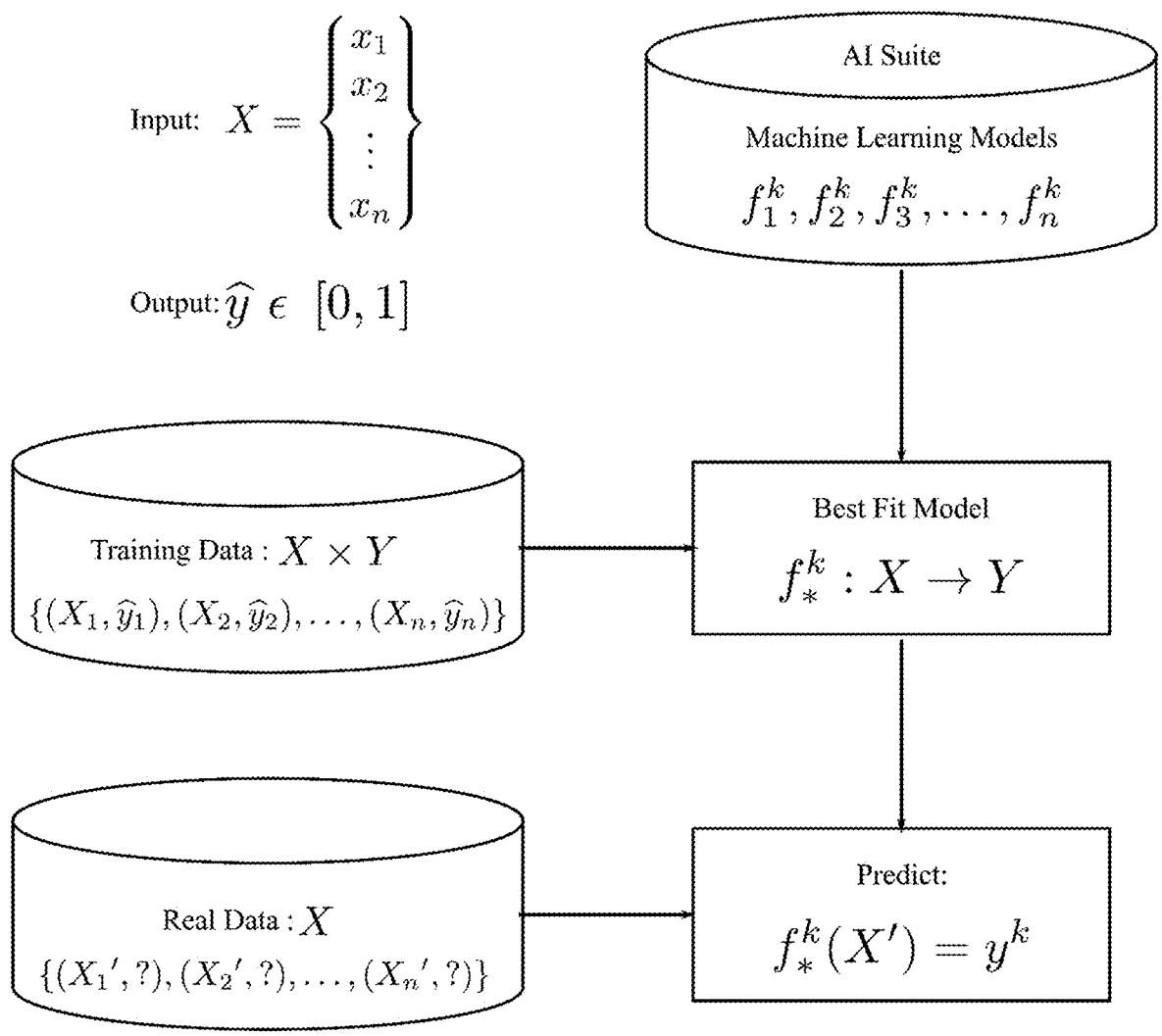
FIG. 3—gives the diagrammatic representation of AI Algorithms that help predict the MIHIC Risk Score, in one embodiment.

55 Obestric History
56 Occupation
57 Owns House
58 Parity
59 Past Illness of Pregnant Women
60 Pin code
61 Platelet count (/mm3)
62 Polio
63 Post Pardinal Blood Sugar
64 Postpartum contraception method
65 Postpartum Haemorrhage
66 Preeclampsia
67 Preterm Labour
68 Prolonged Labour
69 Protein/Creatinine ratio
70 Proteinuria (mg/24)
71 Prothrombin time (plasma) (seconds)
72 Race
73 Retained Placentas
74 Serum creatinine (mg/dL)
75 Serum uric acid (mg/dL)
76 Sexually Transmitted Diseases
77 Site of hospital
78 Skin Rashes
79 Syphilis
80 Systolic Blood Pressure
81 Type of Delivery
82 Typhoid
83 Urine Test for Albumin
84 Urine Test for Sugar
85 Uterus Size
86 Village
87 Visit Frequency
88 Visit Number
89 Weight of Last child born
90 Weight of Pregnant Women The input data of X, $y_i$ is processed by the models for gaining knowledge about a risk. FIG. 3 illustrates computations using knowledge about a risk can be attained from the machine learning models using the data that represents characteristics of all pregnant women and their infants.

For a considered risk k (for example, pre-eclampsia) the AI suite employs 'n' number of machine learning algorithms to learn functions $f_1^k, f_2^k, f_3^k, \cdots, f_n^k$ that can map input X to output y using the data points $\{(X_1, \hat{Y}_1), (X_2, \hat{Y}_2), \cdots (X_n, \hat{Y}_n)\}$. Once the functions are learned by training the algorithms, the AI suite selects $f_*^k: X \rightarrow Y$ that best fits the training data. This selection is evaluated by considering a wide range of machine learning performance metrics. The selected model ($f_*^k(X')=y^k$) will be leveraged for predicting the propensity score $y^k$ the risk 'k' given the real data ($X'_1$, ?) of a pregnant woman.

For understanding the working of AI suite algorithms, consider $f_1^k$ as Logistic Regression technique for modelling the machine learning problem of predicting the risk score. The relation between in the input X and output score y is modelled using—

$$y = f_1^k(X) = \beta_0 + \beta_1 x_1 + \beta_2 x_2 + \cdots + \beta_n x_n$$

During the training, the data $\{(X_1, \hat{Y}_1), (X_2, \hat{Y}_2), \cdots (X_n, \hat{Y}_n)\}$ is passed to the model to learn the parameters (weights) $\beta_0, \beta_1, \beta_2, \ldots \beta_n$. where in $\beta_1$ can be any factor associated with $x_1$ which represents the age, $\beta_2$ can be any factor associated with $x_2$ which represents the economic status and similarly, $\beta_3, \beta_4, \ldots, \beta_n$, represents factors associated with various characteristics of the pregnant women in the training data.

Logistic regression uses the cost function $J(\theta)$ to estimate weights that best fits the training data, given by:

$$J(\theta) = \frac{1}{2} \sum_{i=1}^{m} (f_1(X_i) - y_i)^2$$

Furthermore, logistic regression updates the parameters ($\theta$) by using $\theta \leftarrow \theta - \alpha \nabla J(\theta)$. After reducing error in prediction training will be concluded. Advantage of logistic regression is that it not only provides weights but also their corresponding odds ratio and standard deviation error.

AI suite algorithms can be further explained by considering $f_n^k$ as a deep Neural Network architecture for predicting k risk (for example pre-term labour). For each layer, $\mathcal{Z}_j^{[i]}$ can be calculated using $\mathcal{Z}_j^{[i]} = w_j^{[i]T} A^{[i-1]} + \beta_j^{[i]}$ where i is number of layers for $j^{th}$ observation, A is the input layer, w denotes the weights and $\beta$, the biases. First hidden layer A, will be $\alpha^0 = X$, for second layer it will be output of first hidden layer and so on. Depending upon the position of each layer (hidden or output) appropriate activation function is employed such as, sigmoid $$g(z) = \frac{1}{1 + e^{-z}}$$

or rectified linear unit ReLU $g(\mathcal{Z}) = \max(0, \mathcal{Z})$.

For each observation, loss function $L(\mathcal{Z}, y) = -[y \log(\mathcal{Z}) + (1-y) \log(1-\mathcal{Z})]$ is calculated and for total m number of observations, cost function $$J(w, b) = \frac{1}{m} \Sigma_{i=1}^{m} L(z^i, y^i)$$

is calculated. For each iteration, weights w and biases $\beta$ are updated using the function $$\frac{\partial L(z, y)}{\partial w} = \frac{\partial L(z, y)}{\partial a} \times \frac{\partial a}{\partial z} \times \frac{\partial z}{\partial w} \text{ and}$$

$$\frac{\partial L(z, y)}{\partial \beta} = \frac{\partial L(z, y)}{\partial a} \times \frac{\partial a}{\partial z} \times \frac{\partial z}{\partial \beta}$$

to minimize the cost function.

In the context of medical domain, whenever there can be some uncertainty in inferring the interactions amongst input data, leveraging deep neural networks offers a good solution.

Alternatively, $f_1^k$ can be a Recurrent Neural Network (RNN) that processes the textual data that captures the characteristics of the pregnant women. This textual data is transformed to information represented using vectors that is compatible for processing with other characteristics. Modelling with RNN involves representing data in sequences, the input holding textual data is forwarded to network as $x = (x_1, \ldots, x_L)$ of length 'L'. The output variable y, where $y = (y_1, \ldots, y_m)$ is a sequence of any bounded length m. The RNN network is trained on the data of notation $D = \{(x_{(j)}, y_{(j)})\}^n$, having sample size as n.

At each layer, the propagation of layers in the network can be represented using the following equation $$f: I_h \times I_x \times H_T \rightarrow I_h$$

where $I_x$ represents the product space of input, $I_h$ product space of hidden states and $H_T$ product space of parameters θ. To simplify it, for any given hidden state h, input data x and estimated parameters θ.

$$f(h,x,\theta) \in I_h$$

This RNN is distinct from generic neural network in a way that at any $i^{th}$ layer, the inputs will be from $(i-1)^{th}$ hidden layer. The layers hidden states process by $h_i = f(h_{i-1}, x_i, \theta)$ prediction at the final layer is performed using $\hat{y}_i = (g \circ \alpha_1)$ (h), where in $\alpha_i = f_i \circ \ldots \circ f_1$ with each function $f_i$: $I_h \to I_h$ As every layer of RNN produces an output, loss is to be computed at each layer. Total loss is computed at the final layer as the sum of losses incurred at each layer as $J(\theta) = \Sigma J(y, \hat{y}_i)$ Each value of the vector y, denotes a clinical entity including, but not limited to, symptoms, medical history, age, race, test results etc. In this way, the unstructured information in the documents are extracted and processed along with other characteristics for prediction of risks.

Similarly, $f_4^k$ can also be any popular machine learning algorithms like Support Vector Regression (SVR) having a generic mapping functions, $y = f(X) = w^T X + \beta$ to model the input and output data. SVR has the ability to deal with nonlinear data and delivers a learned hyperplane from the training data. This hyperplane is usually more stable and does not get influenced by small changes in the data characteristics. Structure of the hyperplane is depending upon the selection of kernel, if kernel with high dimensions is chosen then there will be many support vectors resulting in more time for training. During the training, the model will learn support vectors of hyperplane by using the training data and cost function $J(w) = C\Sigma_{i=1}^{N} L(y_i, f(X_i)) + \frac{1}{2}\|w\|^2$, which is an intensive loss function of epsilon. Optimization for getting the best estimates of the parameters using unconstrained optimization $J(w) = C\Sigma_{i=1}^{N}(\varphi_i^+ + \varphi_i^-) + \frac{1}{2}\|w\|^2$, where $\varphi_i^+$, $\varphi_i^-$ denote slack variables.

Figure 4:
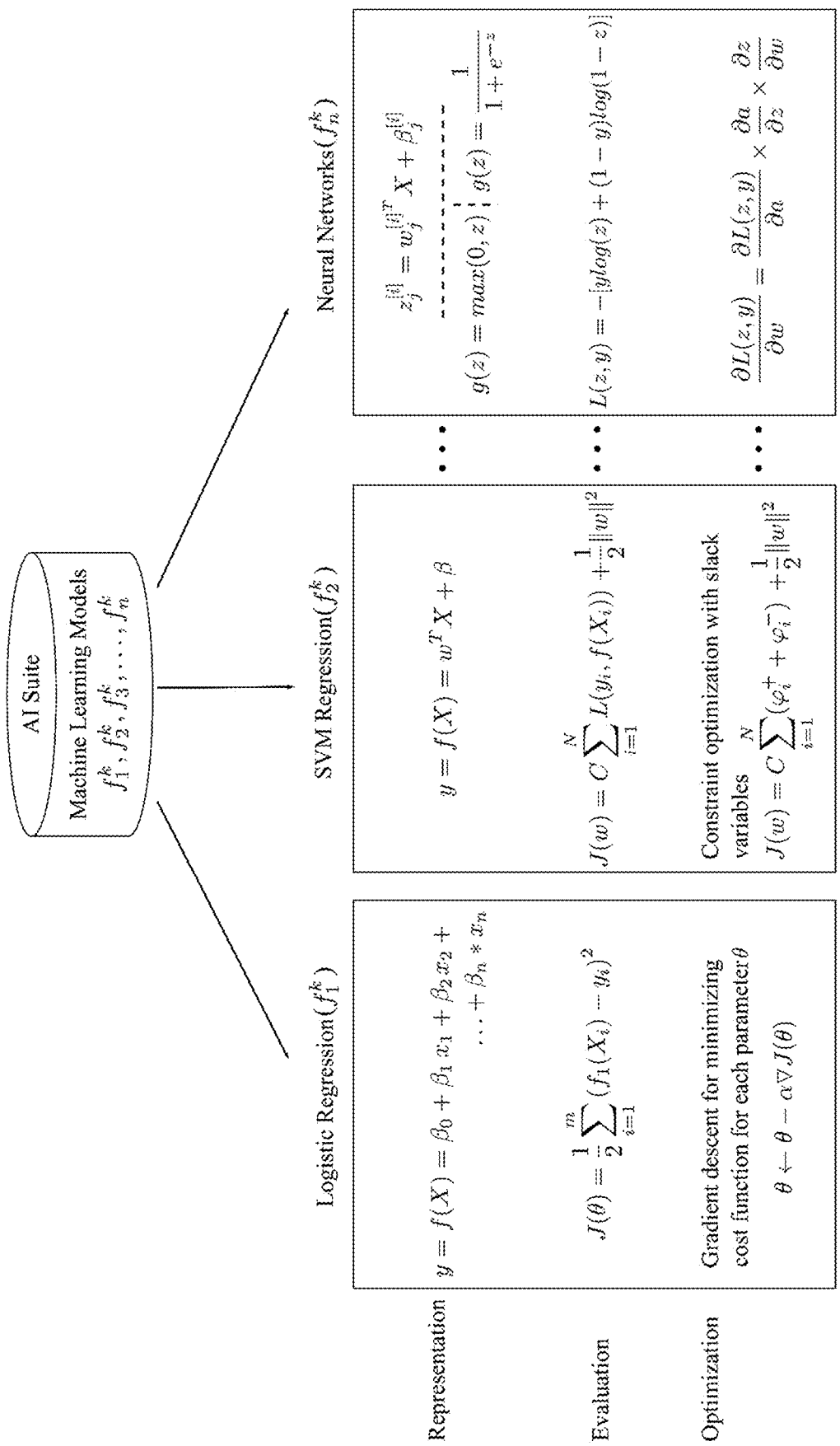
FIG. 4—gives the diagrammatic representation of MIHIC AI Suite's Machine Learning Models, in one embodiment.

As illustrated in FIG. 4, the MIHIC system includes in various embodiments of the claimed invention an AI suite which executes multiple machine learning models to find the optimum model yielding highest metrics of evaluation. The AI suite includes, but is not limited to, models as simple as logistic regression, Support Vector Machine (SVM) regression to complex models such as neural networks including, but is not limited to, convolutional neural network (CNN), recurrent neural network (RNN) and long short-term memory model (LSTM).

In one possible configuration of the system, all available types of input data (depicted in FIG. 2) can be used to train multiple models and best model will be employed for predicting multiple event outcomes related to maternal, fetal and infant health.

In another possible configuration of the system, multiple machine learning model will be trained on subset of data and best ensemble of those models will be employed for the prediction in various embodiments of the claimed invention. For example, CNN model will be trained using image scans data, RNN models will be trained using clinical notes and medical history data and so on. Then best performing models from each input data types will be assessed for concordance among them and then all those models will be ensembled or stacked together to predicting multiple event outcomes related to maternal, fetal and infant health.

Further, the system provides a specific and unique way to predict the maternal, fetal and infant/neonatal risks in pregnant mothers as well as mothers who are planning to become pregnant. It includes a gamut of 48 comprehensive risks covering mother, fetus and infant and can be expand further.

The Maternal risk factors include, but are not limited to, miscarriage, anemia, gestational diabetes, gestational hypertension, preeclampsia, preterm labor, preterm birth, preterm premature rupture of membranes (PPROM), placental abruption, cesarean delivery, sepsis, venous thromboembolic event, postpartum hemorrhage, postpartum depression and multiple births.

Fetal risk factors include, but are not limited to, still birth, growth restriction, macrosomia/excessive growth, congenital anomaly, spina bifida/anencephaly, aneuploidy, drug-induced abnormality, chorioamnionitis/intraamniotic infection and birth injury.

Infant or neonatal risk factors include, but are not limited to, low birth weight, excessive birth weight, neonatal anemia, neonatal hypoglycemia, intraventricular hemorrhage, respiratory distress syndrome, bronchopulmonary dysplasia, necrotizing enterocolitis, retinopathy of prematurity/blindness, neonatal sepsis, neonatal jaundice, neonatal demise, newborn encephalopathy/Hypoxic ischemic encephalopathy (HIE), neurodevelopmental delay/Cerebral Palsy (CP) and admission to NICU (Neonatal Intensive Care Unit).

The MIHIC system goes beyond the pharmacogenomics risk factors and includes additional dimensions including, but not limited to, patient's life-style, demographics, drug-disease and drug-drug interactions to further understand a patient in complete detail and accordingly determine the optimal medical intervention required for each individual patient.

Data points used by the MIHIC system include genomic data (for e.g., genetic variants in CDKAL1 and MTNR1B genes were associated with gestational diabetes mellitus), geographical data (for e.g., The reported Neural Tube defects prevalence ranges and medians for each region vary and were as follows: African (5.2-75.4; 11.7 per 10,000 births), Eastern Mediterranean (2.1-124.1; 21.9 per 10,000 births), European (1.3-35.9; 9.0 per 10,000 births), Americas (3.3-27.9; 11.5 per 10,000 births), South-East Asian (1.9-66.2; 15.8 per 10,000 births), and Western Pacific (0.3-199.4; 6.9 per 10,000 births), BMI (for e.g., obesity can cause preeclampsia, gestational diabetes mellitus, stillbirth), Blood pressure (for e.g., hypertension can cause stillbirth), alcohol intake (for e.g. associated with increased risk of spontaneous abortion), tobacco use (for e.g., tobacco users associated with increased risk of preterm births and stillbirths), rural residence (for e.g., rural residence associated with increased risk of infant mortality).

The MIHIC system not only uses the structured data fields like age, race but also uses unstructured data from sources like clinical reports, social media, audio and video files of patient encounters. It uses a comprehensive list of data fields which include demographic information, clinical data (mother and fetus/infant), routine laboratory tests, investigational biomarkers, genetic testing, transcriptomic/metabolomic/proteomic biomarkers, microbiome, imaging studies (esp. ultrasound), medications, clinical notes—by physicians, nurses, nutritional data, patient experience scores, institutional data—to investigate the impact of practice patterns (for ex. Examining the hospital protocols), physician data (for examining the impact of individual providers on outcome) and audio/video files of Clinician-patient Interactions.

The MIHIC system uses artificial intelligence (AI) techniques with high accuracy of between 75-90% for different individual risk models. The models leverage advanced computing capabilities and are not limited to: Artificial Intelligence (including neural networks, Natural Language Processing and understanding, deep learning) and traditional statistical techniques and can analyze structured and unstructured data sets including, but not limited to: biomarkers and bio-chemistry data, images, genetics, Clinician notes, audios and videos, social media data, demographic and socio-economic data.

The MIHIC system continuously receives real-time feedback from caregivers and improvises the scores on a perpetual basis. It leverages cutting-edge computing capabilities of AI, Mathematics and Statistics, analyzes relevant data (example: genetics, images, Clinician's notes, audio and videos, social media, healthcare records, wearable devices, pathology etc.) and generates unparalleled insights about diseases, their evolution and the impact of interventions.

For example, severe bleeding after birth can kill a healthy woman within hours if she is left unattended. The MIHIC system will enable the Clinicians to identify the women with high risk of severe bleeding post-delivery, based on which preventive steps can be taken, such as injecting oxytocin immediately after childbirth to reduce the risk of bleeding. In another example the MIHIC system helps Clinicians recognize early signs of infection and enables them to prevent or eliminate—through timely treatment—the risks that would otherwise occur due to the progression of such infections.

In another example the MIHIC system enables Clinicians to detect the probability of onset of pre-eclampsia and the same can be managed before the onset of convulsions (eclampsia) and other resulting life-threatening complications with a preventive treatment measure such as administering drugs such as magnesium sulfate for pre-eclampsia, thus lowering a woman's risk.

The MIHIC system provides timely management and preventive treatment that can make the difference between life and death for both the mother and baby.

EXAMPLES

Exemplary System of Maternal Risk

The MIHIC System receives as input in various embodiments of the claimed invention all the demographic, clinical, social, genomic and other omics data about the patient. Including, but not limited to:
 i. Demographic information
 ii. Clinical data (mother and fetus/infant)
 iii. Routine laboratory tests
 iv. Investigational biomarkers
 v. Genetic testing
 vi. Transcriptomic/metabolomic/proteomic biomarkers
 vii. Microbiome
 viii. Imaging studies (esp. ultrasound)
 ix. Medications
 x. (Clinical notes—by physicians, nurses)
 xi. (Nutritional data)
 xii. (Patient experience scores)
 xiii. (Institutional data—to investigate the impact of practice patterns, e.g. Look at hospital protocols)
 xiv. (Physician data—look at the effect of individual providers on outcome)
 xv. Audio/Video files of Clinician-Patient Interactions
 xvi. Data from wearable devices Example 1: Maternal Risk 1—Miscarriage Prediction The MIHIC System consumes the input data and utilizes advanced machine learning and statistical techniques to output a MIHIC score (a value between 0 and 1) which represents the risk of the mother having a miscarriage during the pregnancy. The MIHIC system further stratifies the miscarriage risk as either low, medium or high levels.

Using the MIHIC Miscarriage score and MIHIC level for miscarriage the Clinicians can intervene and prevent miscarriage occurring in the high-risk patients by treating the preventable conditions that lead to miscarriage including, but not limited to, uncontrolled diabetes, uterine abnormalities and avoiding invasive prenatal tests, advising patients against smoking of cigarettes or e-cigarettes, consumption of alcohol and illicit drugs.

Also, healthcare utilization can be driven down by driving interventions only in patients at high risk for miscarriage and not in patients at low risk for miscarriage.

Example 2: Maternal Risk 2—Anemia Prediction

The MIHIC System ingests the input data and utilizes advanced machine learning and statistical techniques to output a MIHIC score (a value between 0 and 1) which represents the risk of the mother having anemia during the pregnancy. The MIHIC system further stratifies the anemia risk as either low, medium or high levels.

Using the MIHIC Anemia score and MIHIC level for anemia, Clinicians can intervene and prevent anemia occurring in the high-risk patients by treating the preventable conditions that lead to anemia including, but not limited to, not consuming enough iron, treat parasite infections, prevent exposure to malarial infection and advise dietary changes that may help prevent morning sickness and vomiting.

Also, healthcare utilization can be driven down by driving interventions only in patients at high risk for anemia and not in patients at low risk for anemia.

Example 3: Maternal Risk 3—Gestational Diabetes Prediction

The MIHIC System consumes the input data and utilizes advanced machine learning and statistical techniques to output a MIHIC score (a value between 0 and 1) which represents the risk of the mother having gestational diabetes during the pregnancy. The MIHIC system further stratifies the gestational diabetes risk as either low, medium or high levels.

Using the MIHIC gestational diabetes score and MIHIC level for gestational diabetes, Clinicians can intervene and prevent gestational diabetes occurring in the high-risk patients by correcting the preventable conditions that lead to gestational diabetes including, but not limited to:
Lifestyle Interventions:
 monitor weight gain in early stages of pregnancy
 monitor blood sugar
 quit smoking of cigarettes or e-cigarettes increased intensity of exercise while pregnant
Dietary Interventions:
 low glycemic index maternal diet
 high fiber diet
 consumption of probiotics
 increased vitamin D in the maternal diet
Pharmaceutical Interventions:
 administration of metformin
 administration of insulin Also, healthcare utilization can be driven down by driving interventions only in patients at high risk for gestational diabetes and not in patients at low risk for gestational diabetes.

Example 4: Maternal Risk 4—Gestational Hypertension Prediction

The MIHIC System consumes the input data and utilizes advanced machine learning and statistical techniques to output a MIHIC score (a value between 0 and 1) which represents the risk of the mother having gestational hypertension during the pregnancy. The MIHIC system further stratifies the gestational hypertension risk as either low, medium or high levels.

Using the MIHIC Gestational Hypertension score and MIHIC level for gestational hypertension, Clinicians can intervene and prevent gestational hypertension occurring in the high-risk patients by treating the gestational hypertension by taking blood pressure medication as prescribed, stay active, eat a healthy diet and avoid smoking of cigarettes or e-cigarettes, consumption of alcohol and illicit drugs.

Also, healthcare utilization can be driven down by driving interventions only in patients at high risk for gestational hypertension and not in patients at low risk for gestational hypertension.

Example 5: Maternal Risk 5—Preeclampsia Prediction

The MIHIC System consumes the input data and utilizes advanced machine learning and statistical techniques to output a MIHIC score (a value between 0 and 1) which represents the risk of the mother having preeclampsia during the pregnancy. The MIHIC system further stratifies the preeclampsia risk as either low, medium or high levels.

Using the MIHIC Preeclampsia score and MIHIC level for preeclampsia, Clinicians can actively intervene and manage preeclampsia occurring in the high-risk patients by:
Pharmaceutical interventions:
  daily dose of aspirin (85 mg) before 16 weeks of pregnancy
  daily calcium supplement (1.5 g to 2 g)
  administration of diuretics
  administration of antihypertensive drugs
  administration of oral beta blockers
Also, healthcare utilization can be driven down by driving interventions only in patients at high risk for preeclampsia and not in patients at low risk for preeclampsia.

Example 6: Maternal Risk 6—Preterm Labor Prediction

The MIHIC System consumes the input data and utilizes advanced machine learning and statistical techniques to output a MIHIC score (a value between 0 and 1) which represents the risk of the mother having preterm labor during the pregnancy. The MIHIC system further stratifies the preterm labor risk as either low, medium or high levels.

Using the MIHIC Preterm labor score and MIHIC level for preterm labor, Clinicians can intervene and prevent preterm labor occurring in the high-risk patients by treating the preventable conditions including, but not limited to:
Pharmaceutical Interventions:
  progesterone supplements for those with a history of preterm labor
    begin supplements at the 16th to 24th week of pregnancy
    continue taking supplements until the 34th week of pregnancy
  17α-hydroxyprogestrone caproate shots for those with a history of preterm birth
  administration of tocolytics to delay delivery
    nifedipine recommended to block calcium channels
Surgical Interventions:
  single embryo transfer for mothers undergoing IVF
  prevent preterm delivery with cervical cerclage
Environmental Interventions:
  ensure mothers avoid strenuous work
  quit smoking of cigarettes or e-cigarettes
  quit the use of illegal substances
  social support and resources for pregnant victims of domestic violence
Also, healthcare utilization can be driven down by driving interventions only in patients at high risk for preterm labor and not in patients at low risk for preterm labor.

Example 7: Maternal Risk 7—Preterm Premature Rupture of Membranes Prediction The MIHIC System consumes the input data and utilizes advanced machine learning and statistical techniques to output a MIHIC score (a value between 0 and 1) which represents the risk of the mother having Preterm Premature Rupture of Membranes during the pregnancy. The MIHIC system further stratifies the Preterm Premature Rupture of Membranes risk as either low, medium or high levels.

Using the MIHIC Preterm Premature Rupture of Membranes score and MIHIC level for Preterm Premature Rupture of Membranes, Clinicians can actively intervene and prevent Preterm Premature Rupture of Membranes occurring in the high-risk patients by treating the preventable conditions that lead to Preterm Premature Rupture of Membranes including, but not limited to, abnormal vaginal discharge, sexual intercourse during pregnancy, smoking of cigarettes or e-cigarettes, anemia, gestational hypertension.

Also, healthcare utilization can be driven down by driving interventions only in patients at high risk for Preterm Premature Rupture of Membranes and not in patients at low risk for Preterm Premature Rupture of Membranes.

Example 8: Maternal Risk 8—Placental Abruption Prediction

The MIHIC System consumes the input data and utilizes advanced machine learning and statistical techniques to output a MIHIC score (a value between 0 and 1) which represents the risk of the mother having placental abruption during the pregnancy. The MIHIC system further stratifies the placental abruption risk as either low, medium or high levels.

Using the MIHIC placental abruption score and MIHIC level for placental abruption, Clinicians can actively intervene and prevent placental abruption occurring in the high-risk patients by treating the preventable conditions including, but not limited to:
  i. Chronic high blood pressure (hypertension)
  ii. High blood pressure during pregnancy, resulting in preeclampsia or eclampsia
  iii. A fall or other type of blow to the abdomen
  iv. Smoking of cigarettes or e-cigarettes
  v. Cocaine use during pregnancy
  vi. Early rupture of membranes, which causes leaking amniotic fluid before the end of pregnancy
  vii. Infection inside of the uterus during pregnancy (chorioamnionitis).

Also, healthcare utilization can be driven down by driving interventions only in patients at high risk for placental abruption and not in patients at low risk for placental abruption.

Example 9: Maternal Risk 9—Caesarian Delivery Prediction

The MIHIC System consumes the input data and utilizes advanced machine learning and statistical techniques to output a MIHIC score (a value between 0 and 1) which represents the risk of the mother having a Caesarian delivery during the pregnancy. The MIHIC system further stratifies the Caesarian delivery risk as either low, medium or high levels.

Using the MIHIC Caesarian delivery score and MIHIC level for Caesarian delivery, Clinicians can better manage Caesarian delivery occurring in the high-risk patients.

Example 10: Maternal Risk 10—Sepsis Prediction

The MIHIC System consumes the input data and utilizes advanced machine learning and statistical techniques to output a MIHIC score (a value between 0 and 1) which represents the risk of the mother having sepsis following delivery. The MIHIC system further stratifies the sepsis risk as either low, medium or high levels.

Using the MIHIC Sepsis score and MIHIC level for Sepsis, Clinicians can intervene and prevent Sepsis occurring in the high-risk patients by treating the preventable conditions including, but not limited to:
  ensure hygiene of facilities
  administration of antibiotic prophylaxis during childbirth
  particular care during C-sections
Pharmaceutical Interventions:
  administration of antibiotic prophylaxis for third and fourth degree perineal tears
  in the case of C-sections, administration of antibiotic prophylaxis before the incision
    first generation cephalosporin or penicillin is preferred
  treatment of preterm prelabor ruptures of membranes with antibiotics
Surgical Interventions:
  in the case of C-sections, clean the vagina with povidone iodine before the procedure
Environmental Interventions:
  ensure hygiene of childbirth facilities
  ensure that water and tools used during childbirth are properly sanitized
Education Interventions:
  train medical workers to recognize signs of maternal sepsis Also, healthcare utilization can be driven down by driving interventions only in patients at high risk for Sepsis and not in patients at low risk for Sepsis.

Example 11: Maternal Risk 11—Venous Thromboembolic Event Prediction

The MIHIC System consumes the input data and utilizes advanced machine learning and statistical techniques to output a MIHIC score (a value between 0 and 1) which represents the risk of the mother having a venous thromboembolic event during the pregnancy. The MIHIC system further stratifies the venous thromboembolic event risk as either low, medium or high levels.

The MIHIC venous thromboembolic event score and MIHIC level for venous thromboembolic event, Clinicians can intervene and prevent venous thromboembolic event occurring in the high-risk patients by treating the preventable conditions that lead to venous thromboembolic event including, but not limited to, hospitalization, infection, hyperemesis, preeclampsia, obesity, caesarean section, major postpartum bleeding, and intrauterine growth restriction or fetal death.

Also, healthcare utilization can be driven down by driving interventions only in patients at high risk for venous thromboembolic event and not in patients at low risk for venous thromboembolic event.

Example 12: Maternal Risk 12—Postpartum Hemorrhage Prediction

The MIHIC System consumes the input data and utilizes advanced machine learning and statistical techniques to output a MIHIC score (a value between 0 and 1) which represents the risk of the mother having a postpartum hemorrhage during the pregnancy. The MIHIC system further stratifies the postpartum hemorrhage risk as either low, medium or high levels.

Using the MIHIC postpartum hemorrhage score and MIHIC level for postpartum hemorrhage, Clinicians can intervene and prevent postpartum hemorrhage occurring in the high-risk patients by treating the preventable conditions including, but not limited to:
  i. Placental abruption
  ii. Overdistended uterus. This is when the uterus is larger than normal because of too much amniotic fluid or a large baby.
  iii. High blood pressure disorders of pregnancy
  iv. Prolonged labor
  v. Infection
  vi. Obesity
  vii. Use of forceps or vacuum-assisted delivery Also, healthcare utilization can be driven down by driving interventions only in patients at high risk for postpartum hemorrhage and not in patients at low risk for postpartum hemorrhage.

Example 13: Maternal Risk 13—Postpartum Depression Prediction

The MIHIC System consumes the input data and utilizes advanced machine learning and statistical techniques to output a MIHIC score (a value between 0 and 1) which represents the risk of the mother having Postpartum depression following delivery. The MIHIC system further stratifies the Postpartum depression risk as either low, medium or high levels. Using the MIHIC Postpartum depression score and MIHIC level for Postpartum depression, Clinicians can actively intervene and prevent Postpartum depression occurring in the high-risk patients by treating the preventable conditions including, but not limited to:
  i. depression
  ii. bipolar disorder
  iii. baby has health problems or other special needs
  iv. difficulty breast-feeding
  v. problems in relationship with spouse or significant others
  vi. have a weak support system
  vii. have financial problems
  viii. The pregnancy was unplanned or unwanted Also, healthcare utilization can be driven down by driving interventions only in patients at high risk for Postpartum depression and not in patients at low risk for Postpartum depression.

Example 14: Maternal Risk 14—Multiple Births Prediction

The MIHIC System consumes the input data and utilizes advanced machine learning and statistical techniques to output a MIHIC score (a value between 0 and 1) which represents the risk of the mother having multiple births during the pregnancy. The MIHIC system further stratifies the multiple births' risk as either low, medium or high levels.

Using the MIHIC multiple births score and MIHIC level for multiple births, Clinicians can intervene and manage multiple births occurring in the high-risk patients.

Also, healthcare utilization can be driven down by driving interventions only in patients at high risk for multiple births and not in patients at low risk for multiple births.

Example 15: Maternal Risk 15—Placenta Previa Prediction

The MIHIC System consumes the input data and utilizes advanced machine learning and statistical techniques to output a MIHIC score (a value between 0 and 1) which represents the risk of the mother having placenta previa during the pregnancy. The MIHIC system further stratifies the placenta previa risk as either low, medium or high levels.

Using the MIHIC placenta previa score and MIHIC level for miscarriage, Clinicians can intervene and manage complications of placenta previa occurring in the high-risk patients including, but not limited to, hemorrhage and shock, fetal distress from lack of oxygen.

Also, healthcare utilization can be driven down by driving interventions only in patients at high risk for placenta previa and not in patients at low risk for placenta previa.

Example 16: Maternal Risk 16—Placenta Accreta/Increta Prediction

The MIHIC System consumes the input data and utilizes advanced machine learning and statistical techniques to output a MIHIC score (a value between 0 and 1) which represents the risk of the mother having placenta accreta/increta during the pregnancy. The MIHIC system further stratifies the placenta accreta/increta risk as either low, medium or high levels.

The MIHIC placenta accreta/increta score and MIHIC level for placenta accreta/increta, Clinicians can intervene and manage the complications of placenta accreta/increta occurring in the high-risk patients including, but not limited to, hemorrhage, disseminated intravascular coagulopathy, lung failure and kidney failure.

Also, healthcare utilization can be driven down by driving interventions only in patients at high risk for placenta accreta/increta and not in patients at low risk for placenta accreta/increta.

Example 17: Maternal Risk 17—Uterine Rupture Prediction

The MIHIC System consumes the input data and utilizes advanced machine learning and statistical techniques to output a MIHIC score (a value between 0 and 1) which represents the risk of the mother having a uterine rupture during the pregnancy. The MIHIC system further stratifies the risk of uterine rupture risk as either low, medium or high levels.

Using the MIHIC uterine rupture score and MIHIC level for uterine rupture, Clinicians can intervene and prevent uterine rupture occurring in the high-risk patients by treating the preventable conditions that lead to uterine rupture including, but not limited to, use of oxytocin, induction of labor.

Also, healthcare utilization can be driven down by driving interventions only in patients at high risk for uterine rupture and not in patients at low risk for uterine rupture.

Example 18: Maternal Risk 18—Admission to ICU Prediction

The MIHIC System consumes the input data and utilizes advanced machine learning and statistical techniques to output a MIHIC score (a value between 0 and 1) which represents the risk of the mother having admission to ICU during the pregnancy. The MIHIC system further stratifies the admission to ICU risk as either low, medium or high levels.

Using the MIHIC admission to ICU score and MIHIC level for admission to ICU, Clinicians can intervene and prevent admission to ICU occurring in the high-risk patients by treating the preventable conditions that lead to admission to ICU including, but not limited to, no/irregular Antenatal care, hypertension, heart disease, fatty liver, gestational diabetes, thrombocytopenia, oligohydramnios.

Also, healthcare utilization can be driven down by driving interventions only in patients at high risk for admission to ICU and not in patients at low risk for admission to ICU.

Example 19: Maternal Risk 19—Maternal Death Prediction

The MIHIC System consumes the input data and utilizes advanced machine learning and statistical techniques to output a MIHIC score (a value between 0 and 1) which represents the risk of the mother having maternal death during the pregnancy. The MIHIC system further stratifies the maternal death risk as either low, medium or high levels.

Using the MIHIC maternal death score and MIHIC level for maternal death, Clinicians can intervene and prevent maternal death occurring in high-risk patients by treating the conditions that lead to maternal death including, but not limited to, hypertension (eclampsia/preeclampsia), severe bleeding, and infections.

Also, healthcare utilization can be driven down by driving interventions only in patients at high risk for maternal death and not in patients at low risk for maternal death.

Exemplary System of Fetal Risk

The MIHIC System receives as input all available demographic, clinical, social, genomic and other omics data about the patient including, but not limited to:

Demographic information
Clinical data (mother and fetus/infant)
Routine laboratory tests
Investigational biomarkers
Genetic testing
Transcriptomic/metabolomic/proteomic biomarkers
Microbiome
Imaging studies (esp. ultrasound)
Medications Clinical notes—by physicians, nurses
Nutritional data
Patient experience scores
Institutional data—to investigate the effect of practice patterns, e.g. Look at hospital protocols
Physician data—look at the effect of individual providers on outcome
Audio/Video files of Clinician-Patient Interactions

Example 20: Fetal Risk 1—Shoulder Dystocia Prediction

The MIHIC System consumes the input data and utilizes advanced machine learning and statistical techniques to output a MIHIC score (a value between 0 and 1) which represents the risk of the child having a shoulder dystocia. The MIHIC system further stratifies the shoulder dystocia risk as either low, medium or high levels.

The significance of MIHIC shoulder dystocia score and MIHIC level for shoulder dystocia, Clinicians can actively intervene and prevent shoulder dystocia occurring in the high-risk patients by treating the preventable conditions that lead to shoulder dystocia including, but not limited to, gestational diabetes, obesity in mother, epidural anesthesia.

Also, healthcare utilization can be driven down by driving interventions only in patients at high risk for shoulder dystocia and not in patients at low risk for shoulder dystocia.

Example 21: Fetal Risk 2—Stillbirth Prediction

The MIHIC System consumes the input data and utilizes advanced machine learning and statistical techniques to output a MIHIC score (a value between 0 and 1) which represents the risk of the mother having a stillbirth during the pregnancy. The MIHIC system further stratifies the stillbirth risk as either low, medium or high levels.

The significance of MIHIC stillbirth score and MIHIC level for stillbirth, Clinicians can actively intervene and prevent stillbirth occurring in the high-risk patients by treating the preventable conditions including, but not limited to:
Maternal Characteristics:
  Smoking tobacco of cigarettes or e-cigarettes or marijuana during or just before pregnancy, or exposure to secondhand smoke during pregnancy
  Using illegal drugs before or during pregnancy
Maternal Medical Conditions:
  Being overweight or obese
  Diabetes before pregnancy
  High blood pressure before pregnancy
Fetal Characteristics:
  Small size in the fetus, given its age (sometimes called small for gestational age [SGA]).
  Also, healthcare utilization can be driven down by driving interventions only in patients at high risk for stillbirth and not in patients at low risk for stillbirth.

Example 22: Fetal Risk 3—Growth Restriction Prediction

The MIHIC System consumes the input data and utilizes advanced machine learning and statistical techniques to output a MIHIC score (a value between 0 and 1) which represents the risk of the mother having a growth restriction during the pregnancy. The MIHIC system further stratifies the growth restriction risk as either low, medium or high levels.

The significance of MIHIC growth restriction score and MIHIC level for growth restriction, Clinicians can actively intervene and prevent growth restriction occurring in the high-risk patients by treating the preventable conditions that lead to growth restriction including, but not limited to, maternal factors [weight (very low and also increased body mass index), smoking of cigarettes or e-cigarettes, use of recreational drugs, gestational hypertension, inherited or acquired thrombophilia, anemia, autoimmune disorders (phospholipid syndrome, lupus erythematosus), antepartum diabetes mellitus, chronic diseases (chronic pulmonary disease, cyanotic heart disease)], fetal factors [congenital infections (Cytomegalovirus, Syphilis, Rubella, Varicella, Toxoplasmosis, Tuberculosis, HIV, Malaria)], adnexal factors [uterine malformations, subchorionic hematoma, extensive villous infarction, marginal or velamentous cord insertion, placental mosaicism]

Also, healthcare utilization can be driven down by driving interventions only in patients at high risk for growth restriction and not in patients at low risk for growth restriction.

Example 23: Fetal Risk 4—Macrosomia Prediction

The MIHIC System consumes the input data and utilizes advanced machine learning and statistical techniques to output a MIHIC score (a value between 0 and 1) which represents the risk of the mother having a fetus with macrosomia during the pregnancy. The MIHIC system further stratifies the macrosomia risk as either low, medium or high levels.

The significance of MIHIC macrosomia score and MIHIC level for macrosomia, Clinicians can intervene and prevent macrosomia occurring in the high-risk patients by treating the preventable conditions that lead to macrosomia including, but not limited to, maternal obesity, maternal diabetes, excessive weight gain during pregnancy, overdue pregnancy.

Also, healthcare utilization can be driven down by driving interventions only in patients at high risk for macrosomia and not in patients at low risk for macrosomia.

Example 24: Fetal Risk 5—Congenital Anomaly Prediction

The MIHIC System consumes the input data and utilizes advanced machine learning and statistical techniques to output a MIHIC score (a value between 0 and 1) which represents the risk of the mother having a fetus with congenital anomaly during the pregnancy. The MIHIC system further stratifies the congenital anomaly risk as either low, medium or high levels.

The significance of MIHIC congenital anomaly score and MIHIC level for congenital anomaly, Clinicians can intervene and prevent congenital anomaly occurring in the high-risk patients by treating the preventable conditions that lead to congenital anomaly including, but not limited to, maternal exposure to certain pesticides and other chemicals, as well as certain medications, alcohol, tobacco and radiation during pregnancy, maternal infections such as zika virus, syphilis and rubella, nutritional deficiency, alcohol consumption.

Also, healthcare utilization can be driven down by driving preventive measures and/or interventions only in patients at high risk for congenital anomaly and not in patients at low risk for congenital anomaly.

Example 25: Fetal Risk 6—Neural Tube Defects Prediction

The MIHIC System consumes the input data and utilizes advanced machine learning and statistical techniques to output a MIHIC score (a value between 0 and 1) which represents the risk of the mother having a fetus with neural tube defects during the pregnancy. The MIHIC system further stratifies the neural tube defects risk as either low, medium or high levels.

The significance of MIHIC neural tube defects score and MIHIC level for neural tube defects, Clinicians can intervene and prevent neural tube defects occurring in the high-risk patients by treating the preventable conditions that lead to neural tube defects including, but not limited to, inadequate intake of folate.

Also, healthcare utilization can be driven down by driving interventions only in patients at high risk for neural tube defects and not in patients at low risk for neural tube defects.

Example 26: Fetal Risk 7—Aneuploidy Prediction

The MIHIC System consumes the input data and utilizes advanced machine learning and statistical techniques to output a MIHIC score (a value between 0 and 1) which represents the risk of the mother having a fetus with aneuploidy. The MIHIC system further stratifies the aneuploidy risk as either low, medium or high levels.

The significance of MIHIC aneuploidy score and MIHIC level for aneuploidy, Clinicians can intervene if aneuploidy occurs in the high-risk patients by diagnosing aneuploidy by prenatal screening.

Also, healthcare utilization can be driven down by driving genetic testing only in patients at high risk for aneuploidy and not in patients at low risk for aneuploidy.

Example 27: Fetal Risk 8—Drug-Induced Abnormality Prediction

The MIHIC System consumes the input data and utilizes advanced machine learning and statistical techniques to output a MIHIC score (a value between 0 and 1) which represents the risk of the mother having a fetus with drug-induced abnormality during the pregnancy. The MIHIC system further stratifies the drug-induced abnormality risk as either low, medium or high levels.

The significance of MIHIC drug-induced abnormality score and MIHIC level for drug-induced abnormality, Clinicians can intervene and prevent drug-induced abnormality occurring in the high-risk patients by avoiding conditions that lead to drug-induced abnormality including, but not limited to, avoiding administration of teratogenic drugs.

Also, healthcare utilization can be driven down by driving interventions only in patients at high risk for drug-induced abnormality and not in patients at low risk for drug-induced abnormality.

Example 28: Fetal Risk 9—Chorioamnionitis/Intraamniotic Infection Prediction

The MIHIC System consumes the input data and utilizes advanced machine learning and statistical techniques to output a MIHIC score (a value between 0 and 1) which represents the risk of the mother having chorioamnionitis/intraamniotic infection during the pregnancy. The MIHIC system further stratifies the chorioamnionitis/intraamniotic infection risk as either low, medium or high levels.

The significance of MIHIC chorioamnionitis/intraamniotic infection score and MIHIC level for chorioamnionitis/intraamniotic infection, Clinicians can intervene and prevent chorioamnionitis/intraamniotic infection occurring in the high-risk patients by treating the preventable conditions that lead to chorioamnionitis/intraamniotic infection including, but not limited to, longer duration of membrane rupture, prolonged labor, internal monitoring of labor, multiple vaginal exams, meconium-stained amniotic fluid, smoking of cigarettes or e-cigarettes, alcohol or drug abuse, immune-compromised states.

Also, healthcare utilization can be driven down by driving interventions only in patients at high risk for chorioamnionitis/intraamniotic infection and not in patients at low risk for chorioamnionitis/intraamniotic infection.

Example 29: Fetal Risk 10—Birth Injury Prediction

The MIHIC System consumes the input data and utilizes advanced machine learning and statistical techniques to output a MIHIC score (a value between 0 and 1) which represents the risk of the mother having a fetus with birth injury during the pregnancy. The MIHIC system further stratifies the birth injury risk as either low, medium or high levels.

The significance of MIHIC birth injury score and MIHIC level for birth injury, Clinicians can intervene and prevent birth injury occurring in the high-risk patients by treating the preventable conditions that lead to birth injury including, but not limited to, macrosomia, prolonged labor, cephalo-pelvic disproportion.

Also, healthcare utilization can be driven down by driving interventions only in patients at high risk for birth injury and not in patients at low risk for birth injury.

Exemplary System of Infant Risk

The MIHIC System receives as input all available demographic, clinical, social, genomic and other omics data about the patient including, but not limited to:
  i. Demographic information
  ii. Clinical data (mother and fetus/infant)
  iii. Routine laboratory tests
  iv. Investigational biomarkers
  v. Genetic testing
  vi. Transcriptomic/metabolomic/proteomic biomarkers
  vii. Microbiome
  viii. Imaging studies (esp. ultrasound)
  ix. Medications
  x. (Clinical notes—by physicians, nurses)
  xi. (Nutritional data)
  xii. (Patient experience scores)
  xiii. (Institutional data—to investigate the effect of practice patterns, e.g. Look at hospital protocols)
  xiv. (Physician data—look at the effect of individual providers on outcome)
  xv. Audio/Video files of Clinicians-Patient Interactions Example 30: Infant Risk 1—Preterm Birth Prediction The MIHIC System consumes the input data and utilizes advanced machine learning and statistical techniques to output a MIHIC score (a value between 0 and 1) which represents the risk of the infant with preterm birth. The MIHIC system further stratifies the preterm birth risk as either low, medium or high levels.

The significance of MIHIC Preterm birth score and MIHIC level for preterm birth, Clinicians can intervene and manage preterm birth occurring in the high-risk patients by treating the preventable conditions in the mother that lead to preterm birth including, but not limited to:
  i. Being overweight or underweight
  ii. Smoking of cigarettes or e-cigarettes or illicit drug use
  iii. Problems with the uterus or cervix
  iv. Uterine or kidney infection
  v. High blood pressure
  vi. Having a lot of stress Also, healthcare utilization can be driven down by driving interventions only in patients at high risk for preterm birth and not in patients at low risk for preterm birth.

Example 31: Infant Risk 2—Low Birth Weight Prediction

The MIHIC System consumes the input data and utilizes advanced machine learning and statistical techniques to output a MIHIC score (a value between 0 and 1) which represents the risk of the mother having an infant with low birth weight. The MIHIC system further stratifies the low birth weight risk as either low, medium or high levels.

The significance of MIHIC low birth weight score and MIHIC level for low birth weight, Clinicians can intervene and prevent low birth weight occurring in the high-risk patients by treating the preventable conditions that lead to low birth weight including, but not limited to, poor maternal nutrition, poor antenatal care, maternal smoking of cigarettes or e-cigarettes, and exposure to known toxic heavy metals such as, lead, mercury, arsenic, cadmium and selenium.

Also, healthcare utilization can be driven down by driving interventions only in patients at high risk for low birth weight and not in patients at low risk for low birth weight.

Example 32: Infant Risk 3—Excessive Birth Weight Prediction

The MIHIC System consumes the input data and utilizes advanced machine learning and statistical techniques to output a MIHIC score (a value between 0 and 1) which represents the risk of the mother having an infant with excessive birth weight during the pregnancy. The MIHIC system further stratifies the excessive birth weight risk as either low, medium or high levels.

The significance of MIHIC excessive birth weight score and MIHIC level for excessive birth weight, Clinicians can intervene and prevent excessive birth weight occurring in the high-risk patients by treating the preventable conditions that lead to excessive birth weight including, but not limited to, maternal diabetes, maternal obesity, excessive weight gain during the pregnancy, overdue pregnancy.

Also, healthcare utilization can be driven down by driving interventions only in patients at high risk for excessive birth weight and not in patients at low risk for excessive birth weight.

Example 33: Infant Risk 4—Anemia Prediction

The MIHIC System consumes the input data and utilizes advanced machine learning and statistical techniques to output a MIHIC score (a value between 0 and 1) which represents the risk of the mother having an infant with anemia during the pregnancy. The MIHIC system further stratifies the anemia risk as either low, medium or high levels.

The significance of MIHIC infant anemia score and MIHIC level for infant anemia, Clinicians can intervene and prevent anemia occurring in infants in high-risk patients by treating the preventable conditions that lead to anemia in infants including, but not limited to, blood loss, maternal diet low in iron, prenatal vitamins, and iron supplements.

Also, healthcare utilization can be driven down by driving interventions only in patients at high risk for anemia in infants and not in patients at low risk for anemia.

Example 34: Infant Risk 5—Hypoglycemia Prediction

The MIHIC System consumes the input data and utilizes advanced machine learning and statistical techniques to output a MIHIC score (a value between 0 and 1) which represents the risk of the mother having an infant with hypoglycemia during the pregnancy. The MIHIC system further stratifies the infant hypoglycemia risk as either low, medium or high levels.

The significance of MIHIC infant hypoglycemia score and MIHIC level for infant hypoglycemia, Clinicians can intervene and prevent hypoglycemia occurring in infants in high-risk patients by treating the preventable conditions that lead to hypoglycemia including, but not limited to, prematurity, small for gestational age, maternal diabetes, perinatal asphyxia, deficient glycogen stores, delayed feeding, hyperinsulinemia.

Also, healthcare utilization can be driven down by driving interventions only in patients at high risk for infant hypoglycemia and not in patients at low risk for infant hypoglycemia.

Example 35: Infant Risk 6—Intraventricular Hemorrhage Prediction

The MIHIC System consumes the input data and utilizes advanced machine learning and statistical techniques to output a MIHIC score (a value between 0 and 1) which represents the risk of the mother having an infant with intraventricular hemorrhage. The MIHIC system further stratifies the intraventricular hemorrhage risk as either low, medium or high levels.

The significance of MIHIC intraventricular hemorrhage score and MIHIC level for intraventricular hemorrhage, Clinicians can intervene and prevent intraventricular hemorrhage occurring in the high-risk patients by treating the preventable conditions that lead to intraventricular hemorrhage including, but not limited to, low birth weight and gestational age, maternal smoking of cigarettes or e-cigarettes, premature rupture of membranes, intrauterine infections, prolonged labor, postnatal resuscitation and intubation, transferal from one unit to another, early onset of sepsis, development of respiratory distress syndrome or pneumothorax, recurrent endotracheal suctioning, metabolic acidosis and rapid bicarbonate infusion, and high-frequency ventilation.

Also, healthcare utilization can be driven down by driving interventions only in patients at high risk for infants with intraventricular hemorrhage and not in patients at low risk for intraventricular hemorrhage.

Example 36: Infant Risk 7—Respiratory Distress Syndrome Prediction

The MIHIC System consumes the input data and utilizes advanced machine learning and statistical techniques to output a MIHIC score (a value between 0 and 1) which represents the risk of the mother having an infant with respiratory distress syndrome during the pregnancy. The MIHIC system further stratifies the respiratory distress syndrome risk as either low, medium or high levels.

The significance of MIHIC respiratory distress syndrome score and MIHIC level for respiratory distress syndrome, Clinicians can intervene and prevent respiratory distress syndrome occurring in the high-risk patients by treating the preventable conditions that lead to respiratory distress syndrome including, but not limited to, prematurity, maternal diabetes, cesarean delivery, asphyxia.

Also, healthcare utilization can be driven down by driving interventions only in patients at high risk for respiratory distress syndrome and not in patients at low risk for respiratory distress syndrome.

Example 37: Infant Risk 8—Bronchopulmonary Dysplasia Prediction

The MIHIC System consumes the input data and utilizes advanced machine learning and statistical techniques to output a MIHIC score (a value between 0 and 1) which represents the risk of the mother having an infant with bronchopulmonary dysplasia during the pregnancy. The MIHIC system further stratifies the bronchopulmonary dysplasia risk as either low, medium or high levels.

The significance of MIHIC bronchopulmonary dysplasia score and MIHIC level for bronchopulmonary dysplasia, Clinicians can intervene and prevent bronchopulmonary dysplasia occurring in the high-risk patients by treating the preventable conditions that lead to bronchopulmonary dysplasia including, but not limited to, prematurity, prolonged mechanical ventilation, administration of high concentration of oxygen, maternal smoking of cigarettes or e-cigarettes or use of illicit drugs, maternal malnutrition, and infections in the mother during the pregnancy, patent ductus arteriosus, intra-uterine growth retardation.

Also, healthcare utilization can be driven down by driving interventions only in patients at high risk for bronchopulmonary dysplasia and not in patients at low risk for bronchopulmonary dysplasia.

Example 38: Infant Risk 9—Necrotizing Enterocolitis Prediction

The MIHIC System consumes the input data and utilizes advanced machine learning and statistical techniques to output a MIHIC score (a value between 0 and 1) which represents the risk of the mother having an infant with necrotizing enterocolitis during the pregnancy. The MIHIC system further stratifies the necrotizing enterocolitis risk as either low, medium or high levels.

The significance of MIHIC necrotizing enterocolitis score and MIHIC level for necrotizing enterocolitis, Clinicians can intervene and prevent necrotizing enterocolitis occurring in the high-risk patients by treating the preventable conditions that lead to necrotizing enterocolitis including, but not limited to, intrauterine growth retardation, polycythemia, hypoglycemia, sepsis, exchange transfusions, umbilical lines, gestational diabetes, and being born to a mother with chorioamnionitis Also, healthcare utilization can be driven down by driving interventions only in patients at high risk for necrotizing enterocolitis and not in patients at low risk for necrotizing enterocolitis.

Example 39: Infant Risk 10—Retinopathy of Prematurity Prediction

The MIHIC System consumes the input data and utilizes advanced machine learning and statistical techniques to output a MIHIC score (a value between 0 and 1) which represents the risk of the mother having an infant with retinopathy of prematurity during the pregnancy. The MIHIC system further stratifies the retinopathy of prematurity risk as either low, medium or high levels.

The significance of MIHIC retinopathy of prematurity score and MIHIC level for retinopathy of prematurity, Clinicians can intervene and prevent retinopathy of prematurity occurring in the high-risk patients by treating the preventable conditions that lead to retinopathy of prematurity including, but not limited to, early gestational age, low birth weight, lower Apgar score and prolonged oxygen therapy.

Also, healthcare utilization can be driven down by driving interventions only in patients at high risk for retinopathy of prematurity and not in patients at low risk for retinopathy of prematurity.

Example 40: Infant Risk 11—Sepsis Prediction

The MIHIC System consumes the input data and utilizes advanced machine learning and statistical techniques to output a MIHIC score (a value between 0 and 1) which represents the risk of the mother having an infant with sepsis during the pregnancy. The MIHIC system further stratifies the sepsis risk as either low, medium or high levels.

The significance of MIHIC sepsis score in infants and MIHIC level for sepsis in infants, Clinicians can intervene and prevent sepsis occurring in the high-risk patients by treating the preventable conditions that can lead to sepsis including, but not limited to:
  i. Maternal GBS colonization (particularly in the setting of inadequate prophylactic treatment),
  ii. Premature rupture of membranes (PROM),
  iii. Preterm rupture of membranes,
  iv. Prolonged rupture of membranes,
  v. Premature birth,
  vi. Maternal urinary tract infection (UTI),
  vii. Chorioamnionitis,
  viii. Maternal fever greater than 38° C. (100.4° F.).

Also, healthcare utilization can be driven down by driving interventions only in patients at high risk for sepsis and not in patients at low risk for sepsis.

Example 41: Infant Risk 12—Jaundice Prediction

The MIHIC System consumes the input data and utilizes advanced machine learning and statistical techniques to output a MIHIC score (a value between 0 and 1) which represents the risk of the mother having an infant with jaundice during the pregnancy. The MIHIC system further stratifies the jaundice risk as either low, medium or high levels.

The significance of MIHIC jaundice in infants score and MIHIC level for jaundice, Clinicians can intervene and prevent jaundice occurring in the high-risk patients by treating the preventable conditions that can lead to jaundice including, but not limited to:
  i. Preterm babies.
  ii. Newborns with feeding difficulties/poor feeding.
  iii. Mother with diabetes.
  iv. Newborns with bruising/cephalohematoma.
  v. Congenital infection.

Also, healthcare utilization can be driven down by driving interventions only in patients at high risk for jaundice and not in patients at low risk for jaundice.

Example 42: Infant Risk 13—Demise Prediction

The MIHIC System consumes the input data and utilizes advanced machine learning and statistical techniques to output a MIHIC score (a value between 0 and 1) which represents the risk of the mother having an infant demise. The MIHIC system further stratifies the demise risk as either low, medium or high levels.

The significance of MIHIC demise score in infants and MIHIC level for demise, Clinicians can intervene and prevent demise occurring in the high-risk patients by treating the preventable conditions that lead to demise including, but not limited to, sepsis, birth asphyxia, respiratory distress syndrome, congenital anomalies.

Also, healthcare utilization can be driven down by driving interventions only in patients at high risk for demise and not in patients at low risk for demise.

Example 43: Infant Risk 14—Newborn Encephalopathy Prediction

The MIHIC System consumes the input data and utilizes advanced machine learning and statistical techniques to output a MIHIC score (a value between 0 and 1) which represents the risk of the mother having an infant with newborn encephalopathy. The MIHIC system further stratifies the newborn encephalopathy risk as either low, medium or high levels.

The significance of MIHIC newborn encephalopathy score and MIHIC level for newborn encephalopathy, Clinicians can intervene and prevent newborn encephalopathy occurring in the high-risk patients by treating the preventable conditions that lead to newborn encephalopathy including, but not limited to, maternal pyrexia, a persistent occipitoposterior position.

Also, healthcare utilization can be driven down by driving interventions only in patients at high risk for newborn encephalopathy and not in patients at low risk for newborn encephalopathy.

Example 44: Infant Risk 15—Neurodevelopmental Delay Prediction

The MIHIC System consumes the input data and utilizes advanced machine learning and statistical techniques to output a MIHIC score (a value between 0 and 1) which represents the risk of the mother having an infant with neurodevelopmental delay during the pregnancy. The MIHIC system further stratifies the neurodevelopmental delay risk as either low, medium or high levels.

The significance of MIHIC neurodevelopmental delay score and MIHIC level for neurodevelopmental delay, Clinicians can intervene and prevent neurodevelopmental delay occurring in the high-risk patients by treating the preventable conditions that lead to neurodevelopmental delay including, but not limited to, prematurity, infections during pregnancy/childbirth.

Also, healthcare utilization can be driven down by driving interventions only in patients at high risk for neurodevelopmental delay and not in patients at low risk for neurodevelopmental delay.

Example 45: Infant Risk 16—Admission to NICU Prediction

The MIHIC System consumes the input data and utilizes advanced machine learning and statistical techniques to output a MIHIC score (a value between 0 and 1) which represents the risk of the mother having an infant with admission to NICU during the pregnancy. The MIHIC system further stratifies the admission to NICU risk as either low, medium or high levels.

The significance of MIHIC admission to NICU score and MIHIC level for admission to NICU, Clinicians can intervene and prevent admission to NICU occurring in the high-risk patients by treating the preventable conditions that lead to admission to NICU including, but not limited to, operative method of birth, elective delivery before 39 weeks either vaginally or by cesarean section, maternal diabetes and hypertension.

Also, healthcare utilization can be driven down by driving interventions only in patients at high risk for admission to NICU and not in patients at low risk for admission to NICU.

Example 46: Infant Risk 17—Length of NICU Stay Prediction

The MIHIC System consumes the input data and utilizes advanced machine learning and statistical techniques to output a MIHIC score (a value between 0 and 1) which represents the risk of the mother having an infant with longer length of NICU stay. The MIHIC system further stratifies the longer length of NICU stay risk as either low, medium or high levels.

The significance of MIHIC length of NICU stay score and MIHIC level for length of NICU stay, Clinicians can intervene and prevent longer length of NICU stay occurring in the high-risk patients by treating the preventable conditions that lead to longer length of NICU stay including, but not limited to, respiratory distress syndrome, bronchopulmonary dysplasia.

Also, healthcare utilization can be driven down by driving interventions only in patients at high risk for longer length of NICU stay and not in patients at low risk for longer length of NICU stay.

We claim:
1. A system comprising:
a processor executing a machine learning model, wherein the machine learning model comprises a neural network comprising a hidden layer;
a database comprising a plurality of patient record data; and
wherein the system is configured to:
acquire, by the processor, the plurality of patient record data from the database, wherein the patient record data comprises a text data and an image data;
identify, by the processor, a data format of the patient record data;
segregate the patient record data into a structured data and an unstructured data;
pre-process, by the processor, the structured data and the unstructured data;
generate, by the processor, the machine learning model;
train, by the processor, the machine learning model with the patient record data;
receive, by the machine learning model, a new patient record data associated with a patient, wherein the new patient record data comprises a demographic data, a first clinical data comprising patient data comprising a patient blood pressure, a second clinical data comprising fetal data comprising a fetal heart rate, a medical data, and a genetic data of the patient, wherein the patient is a maternal woman;

analyze, by the machine learning model, the new patient record data to discover a pattern in the patient record data using the database;

predict, by the machine learning model and based on the pattern, a maternal risk score for each health risk factor of a first plurality of health risk factors associated with the patient, a fetal risk score for each health risk factor of a second plurality of health risk factors associated with a fetus of the patient, wherein the maternal risk scores each represent a probability of a maternity-related healthcare event of the patient and the fetal risk scores each represent a probability of a fetus-related healthcare event of the fetus of the patient;

calculate, by the machine learning model, an overall risk score from the maternal risk score of each of the first plurality of health risk factors and the fetal risk score of each of the second plurality of health risk factors using a statistical technique, wherein the overall risk score is a maternal and infant health insights and cognitive intelligence (MIHIC) score;

receive a feed-back from a clinician relating to an observed healthcare event of the patient or the fetus of the patient;

update the machine learning model with the feed-back; and update the database with the new patient record data; and wherein the machine learning model is a self-learning model comprising a feed-back layer that enables the machine learning model to learn continuously from the new patient record data and the feed-back from the clinician to continually improve the prediction of the maternal risk score of each of the first plurality of health risk factors, the fetal risk score of each of the second plurality of health risk factors, and the overall risk score.

2. The system of claim 1, wherein the patient record data is acquired from at least one of an information system of a clinic, a laboratory, a pharmacy, and a health insurance company.

3. The system of claim 1, wherein the system further predicts infant health risk factors; and wherein one or more of the maternal health risk factors, the fetal health risk factors, and the infant health risk factors comprises one or more of a miscarriage, an anemia, a gestational diabetes, a gestational hypertension, a preeclampsia, a preterm labor, a preterm birth, a preterm premature rupture of membrane, a placental abruption, a caesarean delivery, a sepsis, a venous thromboembolic event, a postpartum hemorrhage, a postpartum depression, multiple births, a still birth, a growth restriction, a macrosomia, an excessive growth, a congenital anomaly, a spina bifida, an anencephaly, an aneuploidy, a drug-induced abnormality, a chorioamnionitis, a intraamniotic infection, a birth injury, a low birth weight, an excessive birth weight, an neonatal anemia, a neonatal hypoglycemia, an intraventricular hemorrhage, a respiratory distress syndrome, a bronchopulmonary dysplasia, a necrotizing enterocolitis, a retinopathy of prematurity, a neonatal sepsis, a neonatal jaundice, a neonatal demise, a new born encephalopathy, a hypoxic ischemic encephalopathy, a neurodevelopmental delay, a cerebral palsy, an admission to neonatal intensive care unit.

4. The system of claim 3, wherein the pre-processing of the patient record data comprises cleaning the patient record data; transform unstructured data to structured data; perform data augmentation; format data for conversion; eliminate stop words, punctuations, non-ascii characters; and identify stem words and perform lemmatization.

5. The system of claim 4, wherein the processor is configured to display the overall risk score.

6. The system of claim 1, wherein the machine learning model comprises at least one of a convolution neural network, a recurrent neural network, a deep neural network, and a stacked neural network.

7. The system of claim 1, wherein the neural network comprises a non-linear activation function to capture a non-linear association with the patient record data.

8. The system of claim 1, wherein the first clinical data further comprises a weight of the patient, urine protein of the patient, and an ultrasound scan of the patient.

9. The system of claim 1, wherein the second clinical data further comprises a fetal movement, and a fetal presentation.

10. The system of claim 1, wherein the system is further configured for stratifying a pregnancy of the patient into high, medium and low risk categories using the MIHIC score.

11. The system of claim 1, wherein the processor is further configured to predict the overall risk score using at least one of a logistic regression, a Support Vector Machine (SVM) regression, a convolutional neural network (CNN), a recurrent neural network (RNN), and a long short-term memory model (LSTM).

12. The system of claim 1, wherein the demographic data comprises at least one of an age, a parity, a race, a socio-economic status, a home owner, an occupation, a lifestyle, a county, and a social network.

13. The system of claim 1, wherein the medical data comprises at least one of a gestational week, a body mass index, a family medical history, a trimester history, a blood pressure, a diabetes mellitus data, a haemoglobin value, a fetal heartrate value, a medical symptom, and a health condition diagnosis.

14. The system of claim 1, wherein the first clinical data further comprises at least one of a urine protein value, a protein ratio, a creatinine ratio, a serum creatinine value, a serum uric acid value, an indirect bilirubin value, a lactate dehydrogenase value, a platelet count, a fibrinogen value, a glucose plasma value, and a prothrombin time-plasma value.

15. The system of claim 1, wherein the processor is further configured to display:
a graphical indicator associated with each of the maternal risk scores and each of the fetal risk scores; and
a chart showing correlation between the first plurality of health risk factors and the second plurality of health risk factors.

16. The system of claim 1, wherein the genetic data comprises at least one of a biomarker vascular endothelial growth factor, a placental growth factor, a sfit-1 soluble fms-like tyrosine kinase 1, and a soluble endoglin.

17. The system of claim 1, wherein the processor is further configured to perform normalization, standardization, and stratification of each of the maternal risk scores, each of the fetal risk scores, and the overall risk score, and classify the overall risk score into low, medium, and high categories.

18. The system of claim 1, wherein higher scores of any of the maternal risk scores, the fetal risk scores, and the overall risk score indicates higher probability of a healthcare event; and wherein lower scores of any of the maternal risk scores, the fetal risk scores, and the overall risk score indicates lower probability of a healthcare event.

19. The system of claim 1, wherein the system is configured to take input from active pregnancy of the maternal woman to provide preventive intervention for an improved pregnancy outcome.

20. A method comprising:
receiving, by a processor, a patient record data associated with a patient, wherein the patient record data comprises a demographic data, a clinical data, a medical data, and a genetic data of the patient, wherein the patient record data comprises a text data and an image data;
identifying, by the processor, a data format of the patient record data;
segregating the patient record data into a structured data and an unstructured data;
pre-processing, by the processor, the structured data and the unstructured data to clean data;
generating a machine learning model, wherein the machine learning model is further trained with the patient record data;
training, by the processor, the machine learning model with the patient record data;
receiving a new patient record data associated with a patient; wherein the new patient record data comprises a demographic data, a first clinical data comprising patient data comprising a patient blood pressure, a second clinical data comprising fetal data comprising a fetal heart rate, a medical data, and a genetic data of the patient, wherein the patient is a maternal woman;
analyzing, by the machine learning model, the new patient record data to discover a pattern in the new patient record data using a database;
predicting, by the machine learning model and based on the pattern, a maternal risk score for each health risk factor of a first plurality of health risk factors associated with the patient, and a fetal risk score for each health risk factor of a second plurality of health risk factors associated with a fetus of the patient, wherein the maternal risk scores each represent a probability of a maternity-related healthcare event of the patient and the fetal risk scores each represent a probability of a fetus-related healthcare event of the fetus of the patient;
calculating, by the machine learning model, an overall risk score from the maternal risk score of each of the first plurality of health risk factors and the fetal risk score of each of the second plurality of health risk factors using a statistical technique;
wherein the overall risk score is a maternal and infant health insights and cognitive intelligence (MIHIC) score;
receiving a feed-back from a clinician relating to an observed healthcare event of the patient or the fetus of the patient;
updating the machine learning model with the feed-back; and
updating the database with the new patient record data; and
wherein the machine learning model is a self-learning model comprising a feed-back layer that enables the machine learning model to learn continuously from the new patient record data and the feed-back from the clinician to continually improve the prediction of the maternal risk score of each of the first plurality of health risk factors, the fetal risk score of each of the second plurality of health risk factors, and the overall risk score.

* * * * *